United States Patent
Binkert

(10) Patent No.: US 7,937,660 B2
(45) Date of Patent: *May 3, 2011

(54) COMPUTER-BASED METHODS AND STRUCTURES FOR STENT-GRAFT SELECTION

(75) Inventor: Christoph A. Binkert, Newton, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2495 days.

This patent is subject to a terminal disclaimer.

(21) Appl. No.: 10/418,391

(22) Filed: Apr. 18, 2003

(65) Prior Publication Data

US 2003/0200120 A1    Oct. 23, 2003

Related U.S. Application Data

(60) Provisional application No. 60/374,248, filed on Apr. 19, 2002.

(51) Int. Cl.
*G06F 13/00* (2006.01)
*G06F 15/00* (2006.01)

(52) U.S. Cl. ........................................ 715/707; 715/764

(58) Field of Classification Search .......... 715/707–711, 715/700, 715, 735–737, 751, 764, 851
See application file for complete search history.

(56) References Cited

U.S. PATENT DOCUMENTS

| 5,830,145 A | * | 11/1998 | Tenhoff | 600/463 |
| 2003/0197734 A1 | | 10/2003 | Binkert et al. | |
| 2004/0049257 A1 | * | 3/2004 | Kaspersen et al. | 623/1.13 |

* cited by examiner

*Primary Examiner* — Cao (Kevin) Nguyen

(57) ABSTRACT

A stent-graft planning system is a web-based system that assists a physician in selecting and ordering the right stent-graft online in real-time. The stent-graft planning system provides a physician with a two-dimensional (2D) graphic model reflecting the individual vessel anatomy, e.g., aneurismal anatomy, and the selected stent graft in that anatomy. By comparing the graphic model with the image of the patient's vessels, the physician can note any dimensions that are inconsistent with the graphic image and problems with the stent-graft placement. Each collected measurement is validated and the physician is warned if the measurement suggests a problem. The stent-graft system automatically generates the most suitable stent graft for an individual patient. After reviewing the selected stent graft in the 2D model, the stent graft can be ordered online.

32 Claims, 29 Drawing Sheets

Order | Zenith Stent Graft page 1 / 2

|  | Cook Record No.: | Units: |
|---|---|---|
| Main body | TFB-x1-y1 | 1 |
| Ipsilateral Iliac leg | TFLE-x2-y2 | 1 |
| Ipsilateral Iliac leg - Extender | – | 0 |
| Contralateral Iliac leg | TFLE-x3-y3 | 1 |
| Contralateral Iliac leg - Extender | TFLE-12-z2 | 1 |
| Additional body | – | 0 |
| Additional leg | – | 0 |
| Additional leg | – | 0 |
| Additional leg | – | 0 |
| Additional leg | – | 0 |
| Patient's ID number: | RS - 01 - 13 - 69 | |
| Ordering physician: | John Doe | |
|  | Doe@dochospital.com | |
| Hospital Order No.: | 18948-52 | |
| Procedure to be performed at: | Doe Hospital | |
| Date of Procedure: | 05-12-02 | |
| Date: | 03-18-02 | |

| | | Specification | Warning |
|---|---|---|---|
| Prox. neck | Lowest renal artery preserved | right main renal artery | |
| | Proximal aortic neck | 20 mm | |
| | Aorta at lowest renal artery | 30 mm | ✓ |
| | Aorta 15 mm below lowest renal artery | 35 mm | |
| | Aorta at aneurysm origin | 35 mm | |
| | Suprarenal angle antero-posterior | > 30° | |
| | Suprarenal angle lateral | 35° | |
| | Neck to aneurysm angle antero-posterior | 31° | |
| | Neck to aneurysm angle lateral | > 30° | |
| | Thrombus | 3 | |
| Aneurysm | Length of lowest renal artery to aortic bifurcation | 79 mm | ✓ |
| | Diameter of aneurysm maximum | 70 mm | |
| | Diameter of aorta at bifurcation | 25 mm | ✓ |
| | Length of lowest renal artery to right internal iliac artery | 120 mm | |
| | Length of lowest renal artery to left internal iliac artery | 135 mm | |
| Iliac | Diameter of right common iliac artery | 90 mm | |
| | No stenosis | – | |
| | Diameter of left common iliac artery | 90 mm | |
| | Stenosis, smallest diameter | 7 mm | ✓ |
| | Diameter of right external iliac artery | 30 mm | |
| | Stenosis, smallest diameter | 10 mm | |
| | Diameter of left external iliac artery | 40 mm | |
| | Stenosis, smallest diameter | 7 mm | ✓ |
| femoral | Diameter of right common femoral artery | 20 mm | |
| | Diameter of left common femoral artery | 25 mm | |
| | Calcification | 2 | |
| | Tortuosity | 1 | |
| | Occluded arteries | right internal iliac | |
| | Stenotic arteries (>50%) | right internal iliac | |

COOK® | stentgraftplanner™     P.O. Box 489 · Bloomington, IN 47402-0489

Fig. 21A

Order | Zenith™ Stent Graft                                              page 2 / 2

| Physician's options | Specification | Warning |
|---|---|---|
| Planned access site for main body | right | |
| Planned main body configuration | straight | |
| Planned aortic oversizing | 5 % | ✔ |
| Planned iliac oversizing | 10 % | |
| Planned landing zone in relation to right internal iliac artery | 20 mm | |
| Planned landing zone in relation to left internal iliac artery | 20 mm | |

| Cook recommended Graft | Size | Record number |
|---|---|---|
| Diameter of main body | 22 mm | TFB-x1-y1 |
| Diameter of contralateral leg | 10 mm | |
| Working length of contralateral leg | 14 mm | TFLE-x2-y2 |
| Contralateral extender | - | |
| Diameter of ipsilateral leg | 12 mm | |
| Working length of ipsilateral leg | 14 mm | TFLE-x3-y3 |
| Ipsilateral extender | 37 mm | TFLE-12-z2 |

| Graft changed | | |
|---|---|---|
| Diameter of main body | 24 mm | TFB-x1-y1 |

COOK® | stentgraftplanner™    P.O. Box 489 · Bloomington, IN 47402-0489

Fig. 21B

Stent-Graft Planner my account ▲ | sign up | login | help | feedback

This page lets you change your preferences and gives you an Overview of your orders. You can change your profile and search for orders.

Preferences for John Doe

| | | | | |
|---|---|---|---|---|
| Login: | john04 | change | over sizing aorta: | 5 %   change |
| Password: | ******** | change | over sizing iliac: | 10 %   change |
| Email: | Doc@doehospital.com | change | ☑ | I wish a reminder email for each patient after 1, 6, 12 and 24 months. |
| Hospital: | Doc Hospital | change | ☑ | Show help pop-up windows. |

Preview treated patients search by ID number or by date: [ ▲ go ]

| Patient's ID number | Date of placement | Follow-up to date in months | Date of Death | Comments | |
|---|---|---|---|---|---|
| MB-03-28-69 | 03-11-02 | 0 | 03-12-02 | yes | update |
| CD-06-23-74 | 02-15-02 | 1 | - | no | update |
| AT-11-16-57 | 01-03-02 | 3 | - | no | update |
| FG-06-19-52 | 03-11-01 | 4 | - | no | update |
| CW-01-05-61 | 02-01-02 | 2 | | | update |

NOTE: please write ID number or date as shown in the following example: MB-03-28-69 or 03-11-02.

home | terms of service | our privacy policy | newsletter subscription | About Stent-Graft Planner

COMPUTER-BASED METHODS AND STRUCTURES FOR STENT-GRAFT SELECTION

RELATED APPLICATIONS

This application claims the benefit of U.S. Provisional Application No. 60/374,248 filed Apr. 19, 2002, entitled "Web Service and Business Model for Correct Stent Graft Selection" and naming Christoph A. Binkert, et al. as inventors, which is incorporated herein by reference in its entirety.

BACKGROUND OF THE INVENTION

1. Field of the Invention

The present invention relates generally to stent graft selection, and more particularly to computer based systems and methods for stent-graft selection.

2. Description of Related Art

Intraluminal devices are known for treating stenosis, stricture, aneurysms and the like. Intraluminal or endoprosthetic grafts are designed as internal bypass devices, which relieve stress from the surrounding vessel wall. Often, a device of this type is percutaneously implanted within the vascular system to reinforce collapsing, partially occluded, weakened or abnormally dilated localized sections of a blood vessel.

The need for repair of an abdominal aortic aneurysm in patients has been recognized for many years. Surgical repair of an abdominal aortic aneurysm has a much higher mortality rate than less invasive techniques using a stent graft.

Typically, in choosing a stent graft for repair of an abdominal aortic aneurysm, a pre-operative imaging modality is used. The four most utilized imaging modalities are contrast aortography (CA), spiral computed tomography (CT), magnetic resonance imaging (MR), and intravascular ultrasonography (IVUS). A physician uses the image to assess the diameter of the aneurysmal portions of the aortic system, the diameter and length of the non-aneurysmal proximal neck for anchoring the stent, the diameter and length of the distal aortic/iliac neck, and the total length of the prosthesis required for spanning the length of the aneurysm with fixation into normal arterial tissue proximally and distally of the aneurysm.

With these measurements, the physician uses information provided concerning a particular stent graft to select a stent graft for a particular patient. The selection of the appropriate stent graft is crucial for a successful treatment. Many factors complicate this selection.

For example, a certain length of a normal arterial segment has to be present to anchor the stent graft. If such a segment is not present, no stent graft should be placed. Most stent grafts stay in place because they are larger in diameter than the native vessel, therefore a certain amount of over sizing is necessary. However, too much over sizing can lead to redundance of the cover material and lead to leakage or narrowing.

A failure to consider one of these factors or an inadvertent error in translating a dimension from the image to a device size can result in selection of an inappropriate stent graft. Similarly, an error is entering measured data on an order form can result in the physician obtaining an inappropriate stent graft. In addition, there is no feedback to the physician concerning the accuracy of the measurements take from the imaging or the relationship of the stent-graft selected to the patient's arteries until the placement is in progress.

Also, the stent graft technology is constantly evolving and the number of stent grafts available is increasing and will continue to increase. These factors further complicate the selection of the best stent graft for the patient.

SUMMARY OF THE INVENTION

The problems associated with collecting measurements for selection of a stent graft and considering all the appropriate information for selection of a stent graft have been solved by using a computer-based stent-graft planning process that collects measurements of vessels in a body using a plurality of graphic user interfaces. As the measurements are collected, the measurement are validated and stored in a computer memory.

If a measurement indicates an unacceptable body configuration or a problem with utilizing a stent graft, a warning is presented on a display screen. Thus, the physician is warned about any adverse findings. The warnings are updated based upon the latest manufacturer and scientific knowledge.

The graphic user interfaces include, for example, data windows for entering measurements and check boxes and pull down menus for providing other information. The graphic user interfaces present a logical order for collecting the measurements and other information and eliminate any confusion as to what information is required for selection of a stent graft. The graphic user interfaces also assure that all the necessary information is collected prior to selection of a stent graft.

To assist in assessing the validity of the measurements entered using the graphic user interfaces, a real-time graphic of the body vessels is presented in at least one of the graphic user interfaces. Initially, the graphic of the body vessels is generated using default dimensions. To assist in identifying the measurement associated with a particular data window in a graphic user interface, a portion of the graphic, which corresponds to a measurement to be entered in that data entry window, is highlighted. Also, to assist in identifying the measurement associated with a particular data window, a dimension arrow is displayed on a portion of the graphic that corresponds to the measurement to be entered in that data entry window.

After a measurement is entered via the data entry window, the graphic of the vessels is changed to reflect the collected measurement. The graphic may also be changed to reflect information input via a pull down menu or a check box in a graphic user interface. Thus, direct visual feedback on collected data is provided to the physician. The physician also selects options and gives preferences that are used in the selection of the stent graft.

When all the necessary measurement and other information have been collected, the measurements, information and physician options are used to automatically suggest a sized stent graft. An image of the suggested stent graft is displayed inserted in the graphic of the vessels in a graphic user interface. This allows the physician to evaluate whether the suggested stent graft is sized properly.

The physician can made changes to the suggested stent graft. If a change would cause a problem, an appropriate warning is presented. If a change affects other parts of the stent graft, those parts are re-sized and a modified suggested stent graft is presented and displayed in the graphic.

When the physician has the desired stent graft, an online order is placed for the stent graft directly with the manufacturer. This avoids data transfer errors from a planning sheet to an order form.

The order information, the stent graft information, and the collected measurement and information are stored in a physician database. The physician database includes selective patient information that is used to generate follow-up notices to the physician.

The stent-graft planning process assures that the correct data and information is collected and validated. The warnings and the direct visual feedback allow the physician to evaluate whether stent-graft placement is appropriate for the patient. The automated stent-graft selection and ordering further reduce the possibilities of errors. All of these and other factors described herein provide increased patient safety.

The information used to validate the measurements collected and used to generate the warnings is based upon manufacturer data for the stent graft and is included in a stent graft database. The manufacturer can update the stent graft database to assure that the latest available information is used in the stent graft selection. As indicated above, these warning are also updated based upon the latest scientific knowledge.

Thus, the computer-based method is implemented on a system that includes a stent-graft planner module, a physician database and a stent-graft database. In one implementation the system is a web-based client-server system. However, another implementation uses a client-server system. In another implementation, the system is a stand-alone system such as a personal computer or a personal digital assistant. Execution of the stent-graft planner module generates the plurality of graphic user interfaces used to collect data and other information used in the automatic stent-graft selection. The physician database includes physician preferences for the stent-graft planning process. The stent-graft database includes manufacturer information for at least one stent graft and scientific knowledge concerning stent-graft selection and placement.

The stent-graft planning process can be used to select a stent graft for placement in any location in a set of vessels in a human or animal body that a stent graft is used. The graphic user interfaces are modified to collect measurements for the set of vessels that are needed to select a stent graft used in the set of vessels. The measurement collection, validation and warnings would be implemented based upon manufacturer and scientific data for the stent graft or grafts that could be selected.

A computer program product comprises a medium configured to store or transport computer-readable code for the stent-graft planning process, or in which this computer-readable code may be embedded. Some examples of computer program products are CD-ROM discs, ROM cards, floppy discs, magnetic tapes, computer hard drives, servers on a network, and carrier waves having the computer-readable code for the stent-graft planning process embedded therein.

Thus, a computer program product has stored thereon computer readable computer code where execution of the computer readable computer code generates a method comprising:

collecting measurements of vessels in a body using a plurality of graphic user interfaces; and using the measurements to automatically suggest a stent-graft for use in said vessels.

In another implementation, a computer program product has stored thereon computer readable computer code wherein execution of the computer readable computer code generates a method comprising:

collecting measurements of vessels in a body using a plurality of graphic user interfaces;

collecting physician's options using at least one graphic user interface;

suggesting automatically a stent-graft for use in the vessels using the measurements of vessels and the physician's options; and generating an order that is transmitted via a computer network to a manufacturer of the stent graft.

Included in the stent-graft planning process, is a computer-based process that receives a value for a parameter used in the stent-graft planning process. The value is checked to determine whether the value is within a range of permitted values for the parameter. If the value is outside the range of permitted values, a user is notified. The value is also checked to determine whether the value is within a range associated with a warning for the stent-graft planning process. If the value is within the range associated with a warning, a warning is provided to the user.

In another implementation, a computer program product has stored thereon computer readable computer code wherein execution of the computer readable computer code generates a method comprising:

receiving a value for a parameter used in a stent-graft planning process;

checking the value to determine whether the value is within a range of permitted values for the parameter; and checking the value to determine whether the value is within a range associated with a warning for the stent-graft planning process.

Also included in the stent-graft planning process is a computer-based graphic user interface that is used in the stent-graft planning process. The graphic user interface includes a real-time graphic region and a data entry region for an active stent-graft planning step. Values for parameters used in the active stent-graft planning step are entered using features of the data entry region including data windows, pull down menus and check boxes.

The data entry region optionally includes a data entry progress indicator region. The data entry progress indicator region includes a plurality of indicators for informing a user of the data being entered and the sequence of data entry for a stent-graft planning step.

The computer-based graphic user interface also includes a stent-graft planning progress guide region. The stent-graft planning progress guide region includes a plurality of indicators with each indicator representing a different step in the stent-graft planning process. For example, the plurality of indicators includes a measurement indicator, a physician's options indicator, a graft selection indicator, and an on line order indicator.

The computer-based graphic user interface for a stent-graft planning process still further includes a navigation region for the stent-graft planning process. The navigation region includes a continue button and a sign-out button. Computer program code for the graphic user interface is included in a computer program product and execution of the computer program code generates all or parts of the graphic user interface.

BRIEF DESCRIPTION OF THE DRAWINGS

FIGS. 21A and 21B are an example of a stent-graft order that is generated for an on line order.

FIG. 23 is an example of a my account graphic user interface displayed on a display device.

Figure 1:
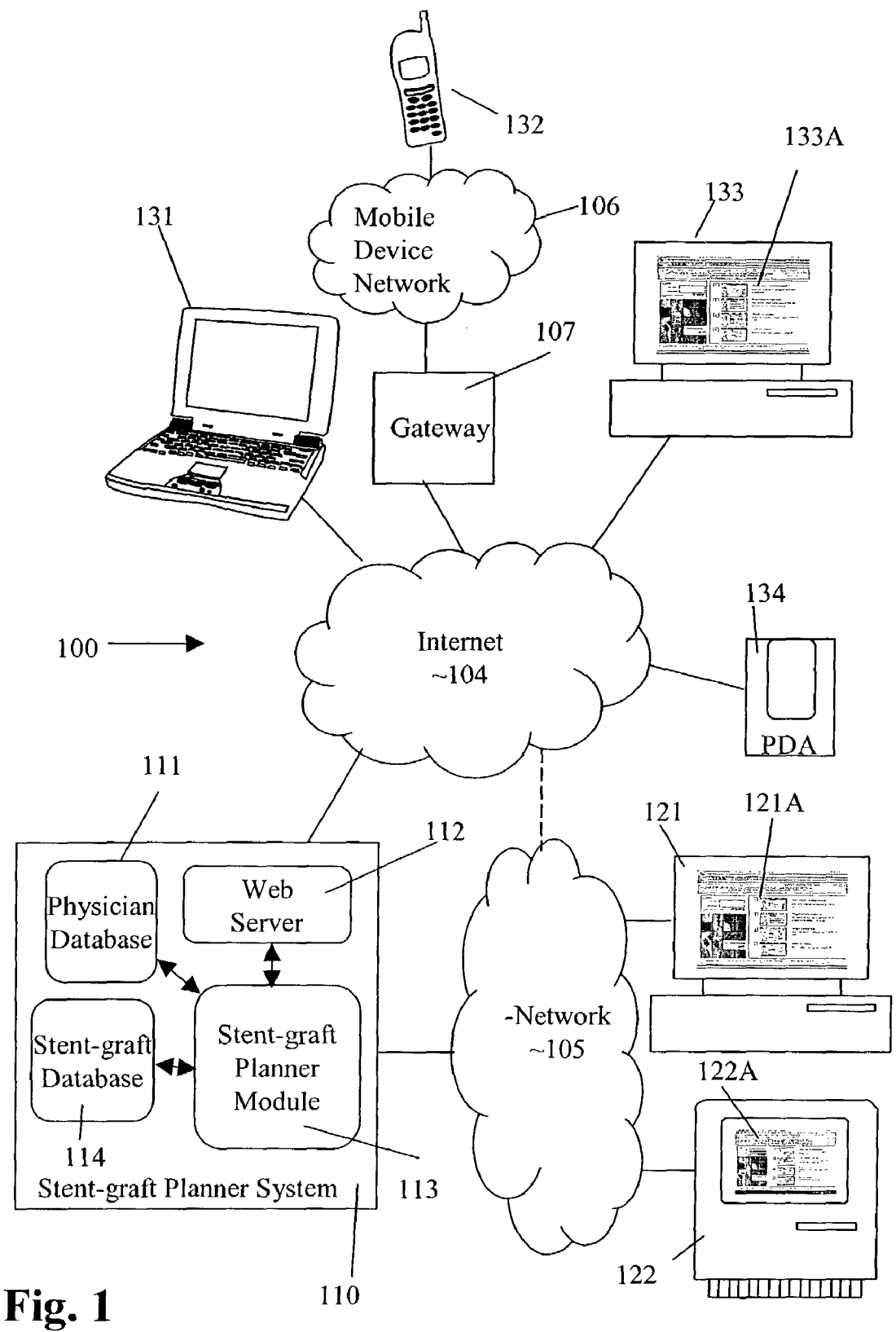
FIG. 1 is an illustration of a system that includes a stent-graft planning system for stent-graft selection.

In the drawings and the following detailed description, elements with the same reference numeral are the same or equivalent elements. For a three-digit reference numeral, the first digit, and for a four-digit reference numeral, the two digits are the figure number in which the element corresponding to the reference numeral first appears.

DETAILED DESCRIPTION

A stent-graft planning system 110 is a web-based system that assists a physician in selecting and ordering the right stent-graft online in real-time. Alternatively, the system maybe implemented on a stand-alone device this is connected to Internet 104.

As explained more completely below, stent-graft planning system 110 provides a physician with a two-dimensional (2D) model and/or a three-dimensional (3D) graphic model reflecting the individual vessel anatomy, e.g., aneurismal anatomy, in which the stent graft will be placed. The graphic model, sometimes called graphic, is adjusted to reflect the measurements collected in stent-graft planning system 110 via graphic user interfaces.

By comparing the graphic with the image of the patient's vessels, the physician can note any dimensions that are inconsistent with the image of the patient's vessels. In addition, each measurement that is entered, i.e., collected, is validated and the physician is warned if the measurement suggests a problem with the patient's anatomy, or with the stent-graft placement.

When a stent graft is selected by system 110 from stent-graft database 114 based upon the collected measurements and physician options, the stent graft is included in the graphic of the patient's vessels based upon the dimensions collected. This allows the physician to evaluate whether the stent graft is suitable for use in the patient. The collected measurements, the patient information, the selected stent graft data, and the physician's preferences used in choosing the stent graft are stored in physician database 111.

Each physician has a personal database, within physician database 111. An option is available for automatic follow-up reminders for the patients in the physician's database.

A physician, sometimes called a user, can access stent-graft planning system 110 via Internet 104 using a portable computer 131, a mobile device 132, a workstation 133, or a personal digital assistant 134 for example. Of course, any device that can connect to the Internet, can display an interface, and can accept data input can be used. This flexibility allows the physician to access stent-graft planning system 110 from a clinic, from an office, from a hospital, from a hospital, a university, or even from home. Consequently, the physician has access to the stent-graft data and information whenever it may be needed. This provides a new level of flexibility and enhances effective use of the physician's time.

Alternatively, a physician can access stent-graft planning system 110 via a network 105, which can be a local area network, a wide area network, or an enterprise network, etc, using a device 121, 122 connected to network 105. Rather than being connected directly to stent-graft planning system 110, network 105 can also be coupled to stent-graft planning system 110 via Internet 104.

Figure 2:
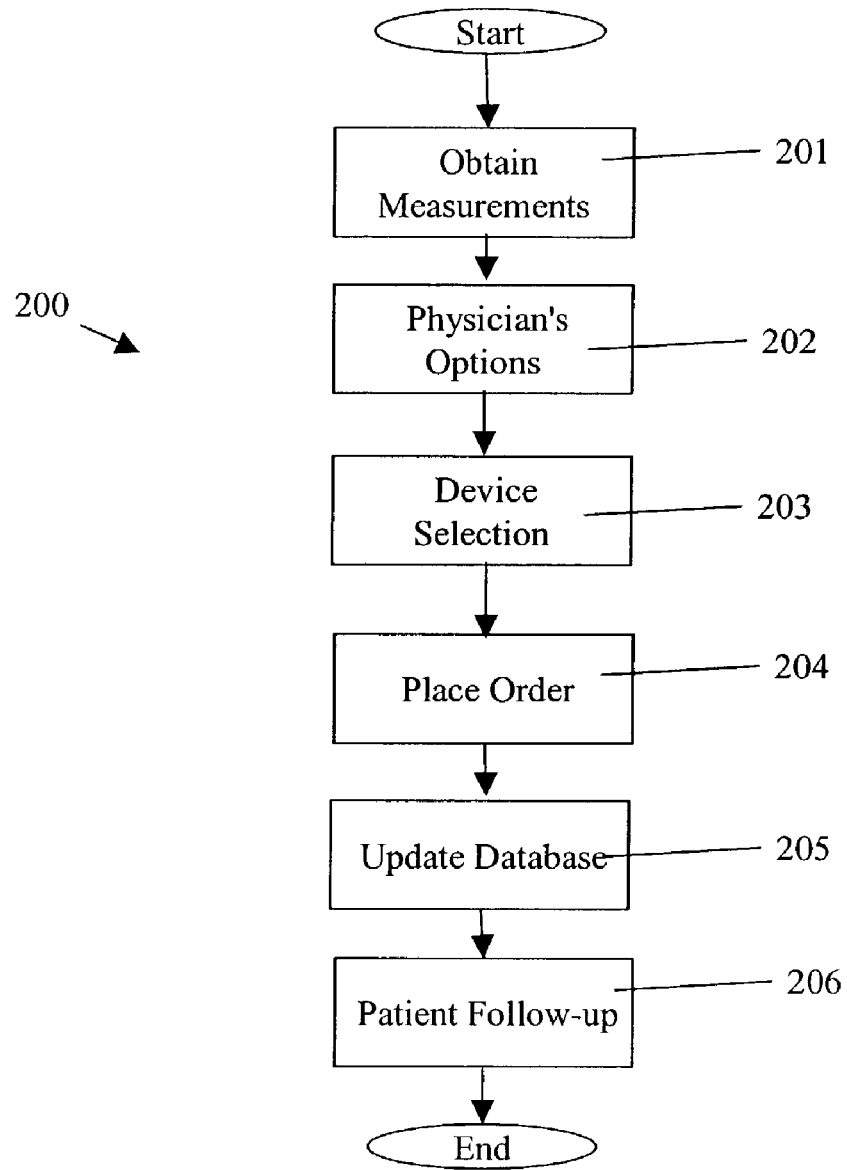
FIG. 2 is a process flow diagram for a stent-graft selection process that can be performed using the web-based stent-graft planning system, using a client-server system, or using a stand-alone system.

Stent-graft planning system 110 generates graphic user interfaces 133A, 121A, 122A that are intuitive and easy to use. Specifically, when stent-graft planner module 113 is executed using web server 112, the physician uses a plurality of graphic user interfaces in a stent-graft planning process 200 (FIG. 2).

In obtain measurements process 201, a physician is provided with a series of graphic user interfaces that guide the physician through inputting the dimensions from the image of the patient that are needed in the stent-graft planning process. A graphic on the graphic user interface provides the physician with a visualization in real-time of the measurements collected. This gives the physician the ability to double-check the measurements.

The measurements and other data entered via the graphic user interfaces are electronically captured, processed, and stored in physician database 111. The graphic user interfaces reduce mistakes in stent-graft planning process 200. The graphic user interfaces help avoid redundancies during measurements and warn about possible problems, i.e., adverse findings, in stent-graft planning process 200. Some or all of the warnings are provided by the stent-graft manufacturer and are incorporated in stent-graft database 114. Also, the warnings are updated and recommendations made according to the latest scientific knowledge.

When obtain measurement process 201 is completed, processing transfers to physician's options operation 202. In operation 202, the physician specifies the planned access site for the main body, the planned main body configuration, and planned landing zones for the stent graft. The physician also specifies aortic and iliac over sizing. This information is also saved in physician database 111.

Upon completion, physician's options operation 202 transfers to device selection operation 203. Device selection operation 203 automatically selects a suggested stent graft from stent-graft database 114, based upon the collected measurements and other information provided by the physician. This makes it easier for the physician and helps to avoid mistakes in stent-graft planning process 200.

The suggested stent-graft is presented to the physician along with a visualization of the stent-graft in place in the patient via a graphic user interface. The physician is allowed to alter the stent-graft selection, as the physician deems appropriate, via another graphic user interface. However, the physician is also provided with any warning or recommendations on such changes as provided by the manufacturer or based upon scientific knowledge.

This automated stent-graft selection process assists the physician because the selection considers factors and makes recommendations based upon the latest manufacturer's data and the latest scientific knowledge. It removes the danger that the physician may make a selection based upon information that is no longer valid, or has been modified to consider factors unknown to the physician.

Finally, when the physician is satisfied with the stent-graft selection, place order operation 204 allows a physician to place an order on-line directly with a manufacturer of the selected stent-graft. The manufacturer is provided with a detailed report of the dimensions, factors, etc, used by the physician in selecting the device or devices in the order.

This report provides data for double-checking the appropriateness of the selected device by the manufacturer. The on-line ordering process simplifies the ordering process, and provides the manufacturer with a standardized format for the process. In addition, this ordering process eliminates the possibility of data transfer errors from a planning sheet to an order form.

Following place order operation 204, or at any other point in process 200 that the physician decides to terminate the current planning process, update database operation 205 saves the data entered in physician database 111. If the physician enters data requesting notification of patient follow-ups, patient follow-up operation 206 reminds the physician via the graphic user interface, e-mail, or fax, for example of the dates for patient follow-up.

The manufacturer can provide new recommendations or new models that can be implemented immediately in stent-graft database 114 of stent-graft planning system 110 and thereby assure that physicians are using the most up-to-date information in selection of a device. Finally, stent-graft planning system 110 can be used as a training tool for both physicians and sales personnel in the factors that are considered in the stent-graft selection process.

Figure 3:
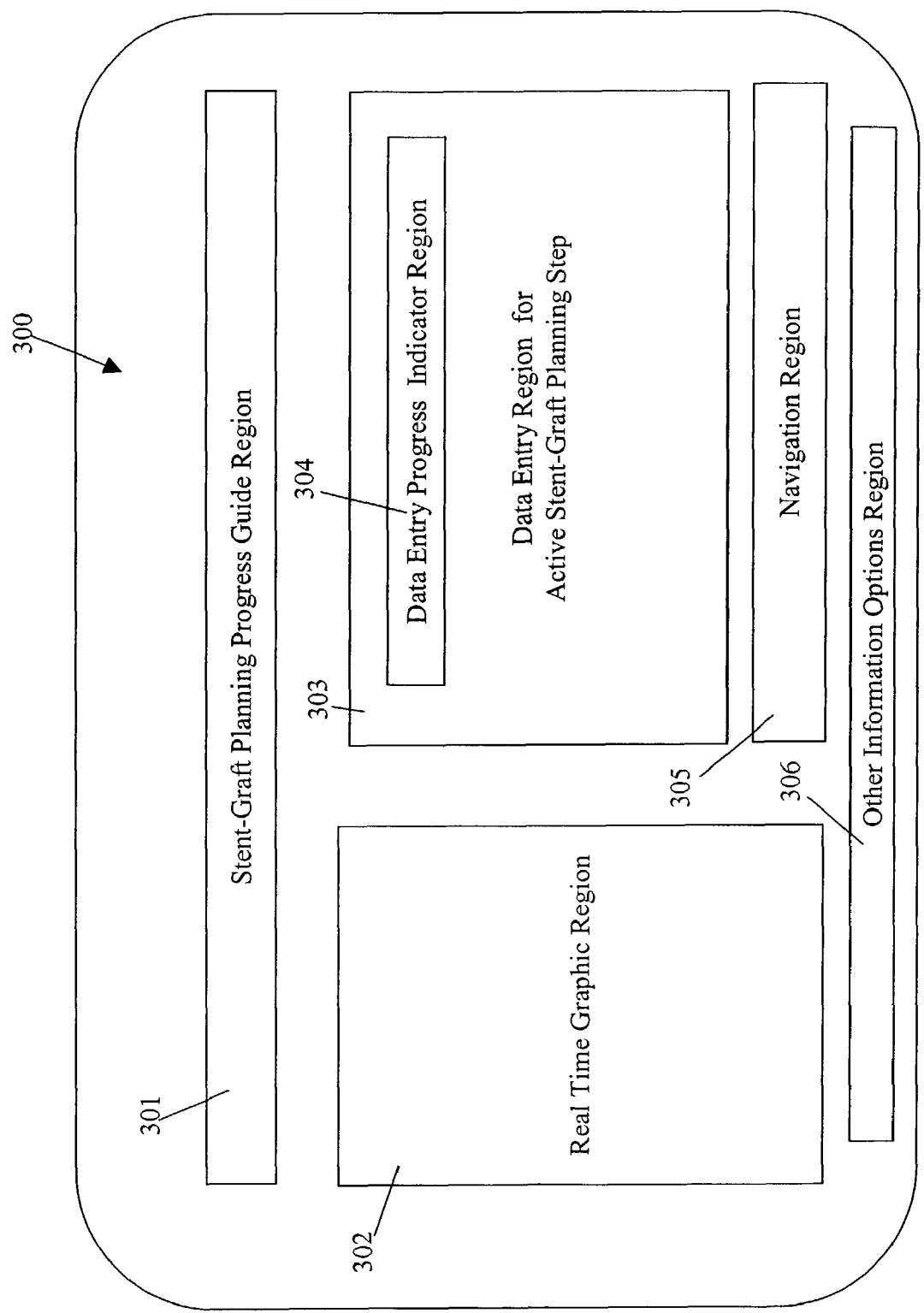
FIG. 3 is for a format for a graphic user interface used in the stent-graft selection process.

A series of screen shots of graphic user interfaces are described below. The graphic user interfaces are presented on a display 400. The graphic user interfaces are used in one implementation of stent-graft planning process 200. FIG. 3 is a representation of a format of a graphic user interface 300 that is used in some of the graphic user interfaces of this example.

Graphic user interface 300, in this example, includes a stent-graft planning progress guide region 301, a real-time graphic region 302, a data entry window for active stent-graft planning step region 303 includes an optional data entry progress indicator region 304, a navigation region 305, and an other information region 306. The use and placement of these regions is illustrative only and is not intended to limit the invention to the specific layout of FIG. 3. Typically, each graphic user interface also includes a title and a brief description of the graphic user interface.

Stent-graft planning progress guide region 301 includes an indicator for each of steps 201 to 204 in stent-graft planning process 200, e.g., a plurality of stent-graft planning progress indicators. For example, the indicators are: 1) Aneurysm measurement; 2) Physician's options; 3) Graft Selection; and 4) Online order. The current step indicator is highlighted. Herein, a step includes one or more operations, as described more completely below.

Data entry region for active stent-graft planning step region 303 provides an interface for entering data. Data entry progress indicator region 304 includes, as appropriate, indicators for informing the physician of the data being entered and the sequence of data entry. This allows the physician to understand the data entry sequence.

Real-time graphic region 302 initially presents a graphic for a default aneurysm for this example. In general, real-time graphic region 302 presents a graphic of the vessels associated with the stent-graft placement, and after selection, an image of the stent-graft positioned in those vessels.

As measurement data is entered in data entry region 303 and validated, e.g., collected, the graphic is modified to reflect the measurement data collected. This can be done either data entry by data entry, after a set of data are entered, or after all the data in region 303 are entered. The important aspect is to provide the physician with a graphic representation of the measurement data so the physician can see when an erroneous entry has been made when compared to the patient's image of the same vessels.

Navigation region 305 includes buttons or other features for navigation of process 200. For example, navigation region 305 includes a sign out button and a continue button. The continue button, for example, is activated only when valid data is entered in all data windows and menus in data entry region 303.

Other information options region 306 provides links for accessing other features of the stent-graft planning site. For example, this region may contain links to home, terms of service, a privacy policy, a newsletter subscription, etc.

Figure 4:
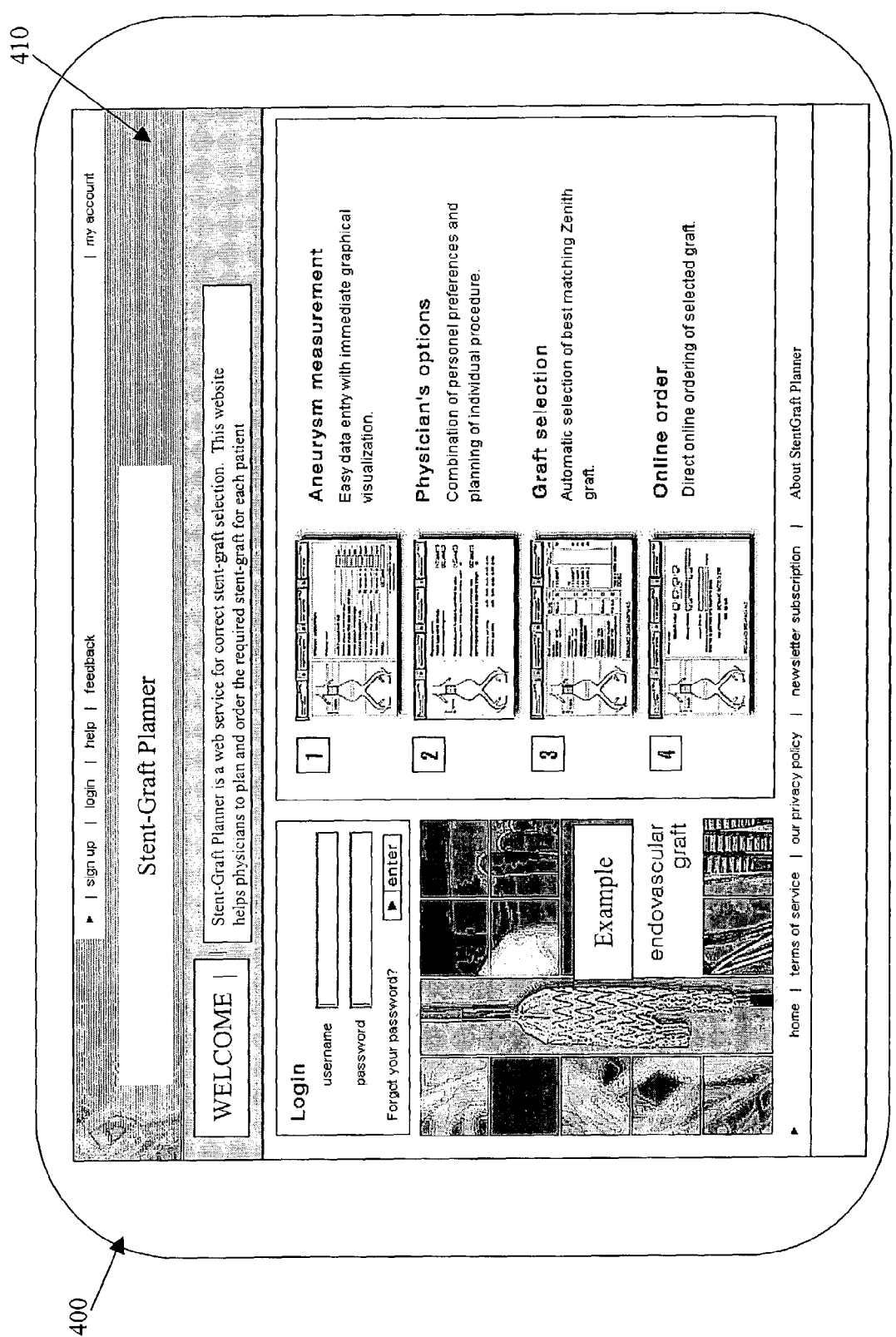
FIG. 4 is an example of an opening graphic user interface displayed on a display device.

FIG. 4 is an illustration of an opening graphic user interface 410 (FIG. 4) on display 400 when a user first visits the stent-graft planning site. The particular format of opening graphic user interface 410 is not essential to this invention. Typically, opening graphic user interface 410 includes information indicating the name of the site, a welcome, a login option, and other descriptive information concerning the site. In this example, the four steps in the planning process are illustrated. In another example, the user could be presented with choices on the various stent-graft selection procedures supported by the site.

Figure 5:
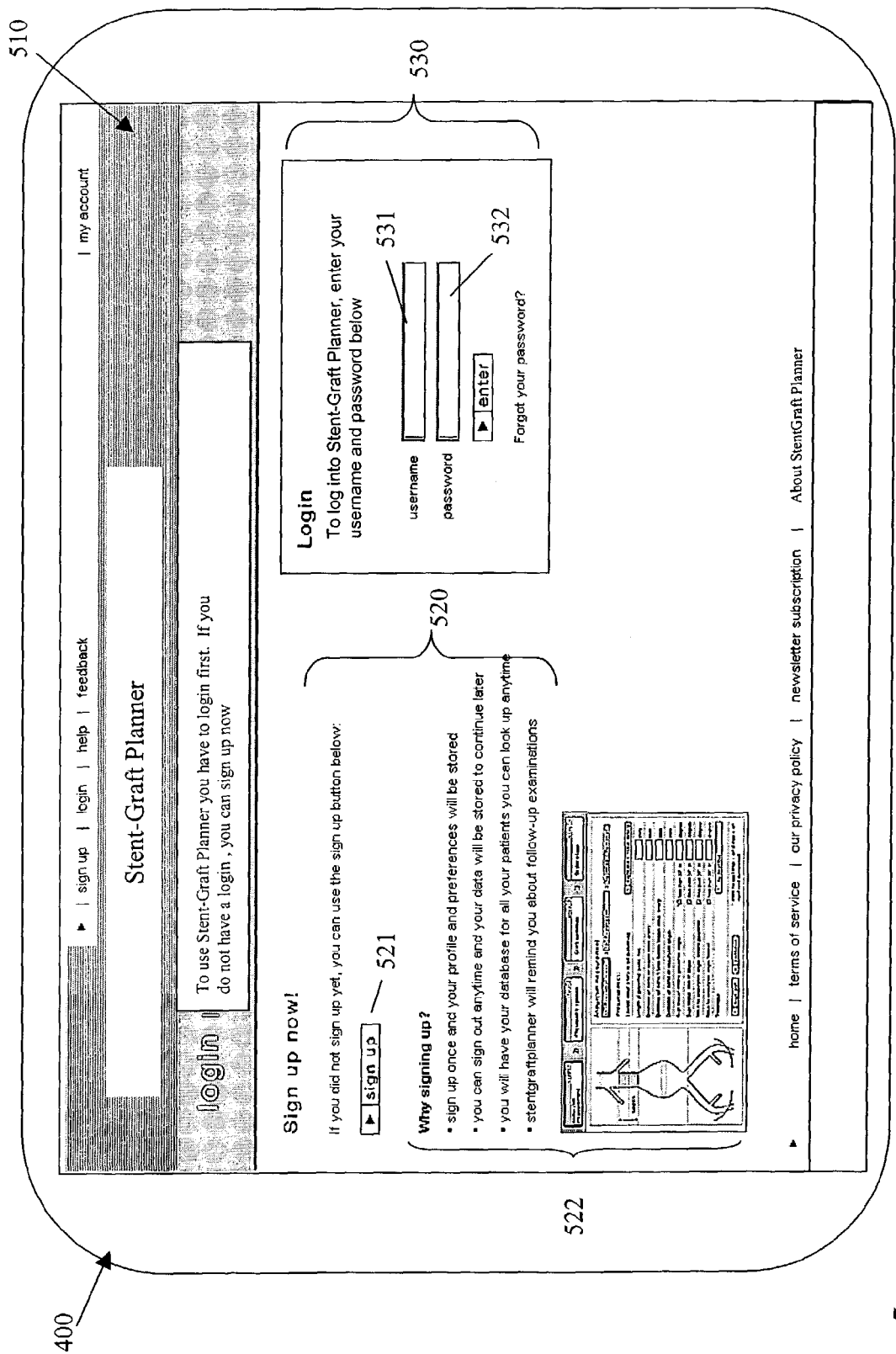
FIG. 5 is an example of a login graphic user interface displayed on a display device.

When a user selects a feature of opening graphic user interface 410, a login graphic user interface 510 (FIG. 5) is presented on display 400. Herein, when it is said that a user selects a feature this means that the user activates a device that causes the selection, e.g., clicks or double-clicks a mouse, depresses a key or combination of keys on a keyboard or touch pad, touches a touch-screen, speaks into a voice recognition system etc.

In this example, login graphic user interface 510 includes a login region 530 with a username window 531 and a password window 532, and a sign up region 521. Sign up region 520 includes a sign up button 521 and a description 522 of the advantages of signing-up at the stent-graft planning site. Login graphic user interface 510 also includes the name of the site and a description of interface 510.

Figure 6:
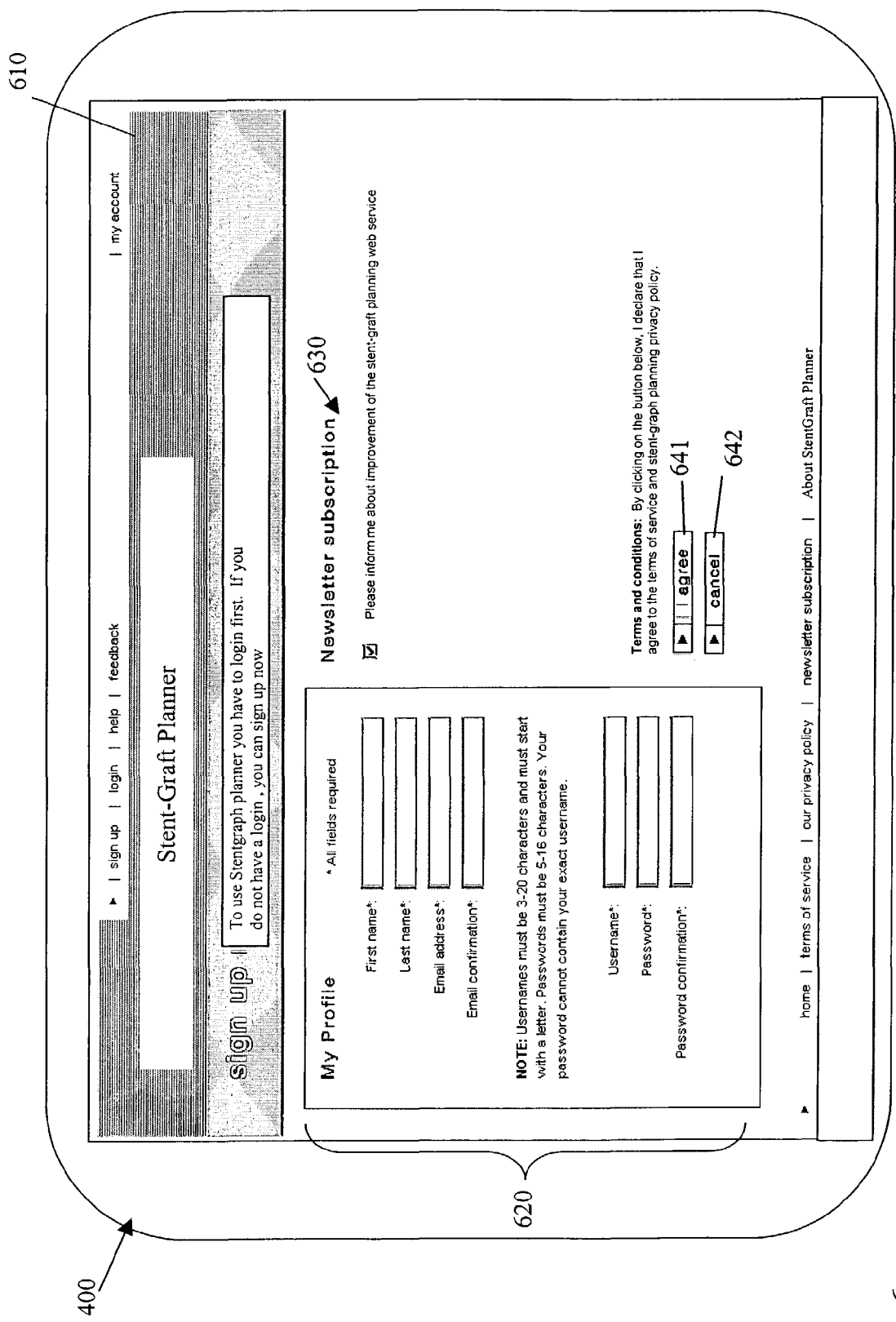
FIG. 6 is an example of a sign up graphic user interface displayed on a display device.

Assuming the user selects sign up button 521, sign up graphic user interface 610 (FIG. 6) is presented on display 400. Sign up graphic user interface 610 includes a profile region 620 where the user supplies a first name, last name, e-mail address, a username and a password. A newsletter subscription option 630 is included with a default value of selected. Finally, an agree button 641 and a cancel button 642 are used to indicate whether the user accepts the privacy policy and any terms of service associated with using the stent-graft planner site. Sign up graphic user interface 610 also includes the name of the site and a description of interface 610. Unless the user provides all the information in profile region 620 and selects agree button 641, further access to the stent-graft planner site is denied.

When a user successfully logs in, the user data is saved in physician database 111. The user also selects a stent-graft family from the manufacturer from which the user wants to select a particular sized stent graft using process 200.

Figure 7:
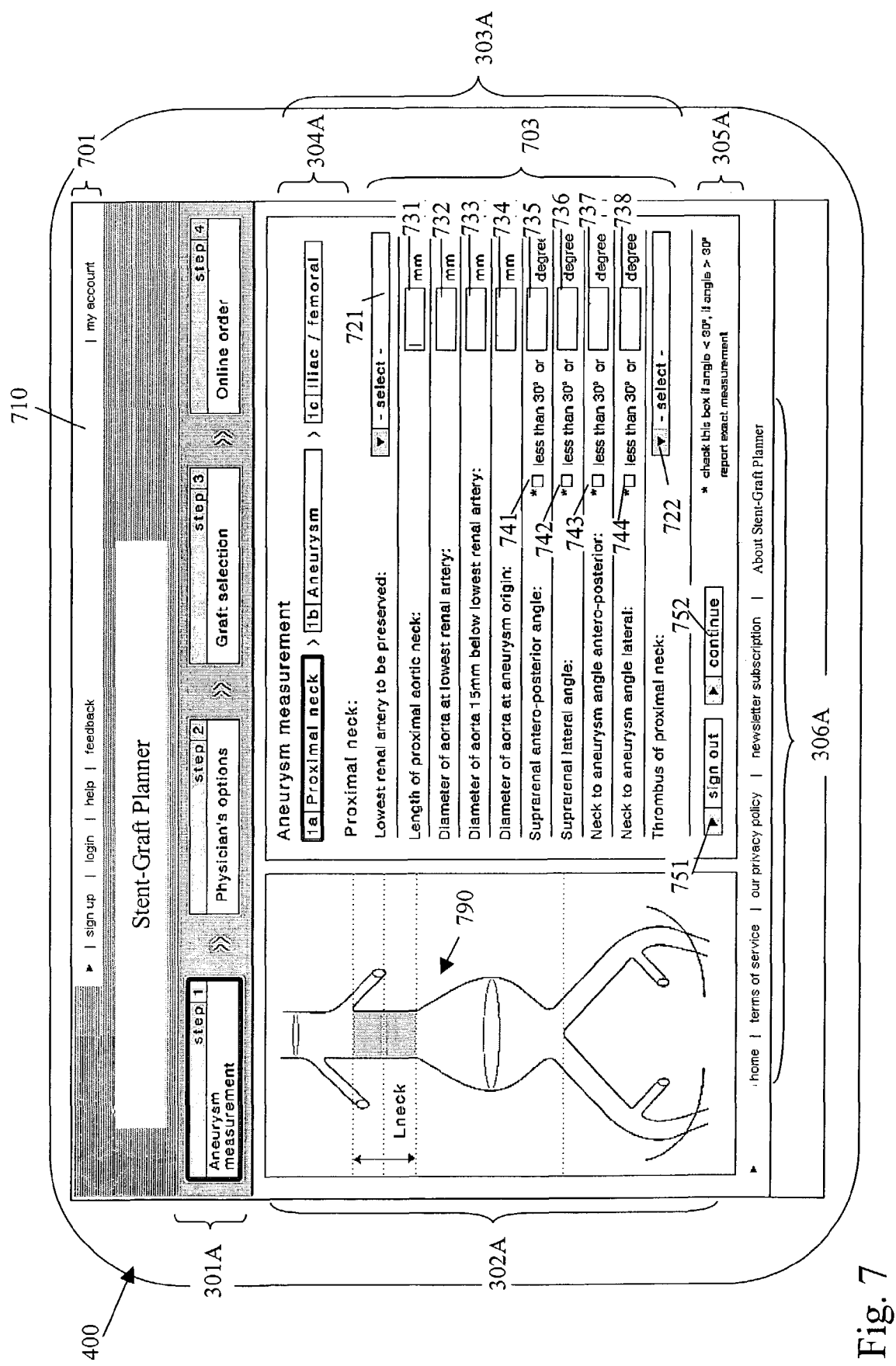
FIG. 7 is an example of an aneurysm proximal neck graphic user interface displayed on a display device.

The user is presented, in this example, with aneurysm proximal neck graphic user interface 710 (FIG. 7). Aneurysm proximal neck graphic user interface 710 includes each of the regions as described above for FIG. 3, i.e., regions 301A, 302A, 303A, 304A, 305A, 306A. In FIG. 7, an "A" is added to the reference numeral of FIG. 3 to indicate that FIG. 7 presents a specific example of the regions in FIG. 3.

In this example, other information options region 306A includes links to home, terms of service, our privacy policy, newsletter subscription and about Stent-Graft Planner. Another information options region 701 includes links to sign up, login, help, feedback, and my account.

In stent-graft planning progress guide region 301A, four steps are illustrated, aneurysm measurement step 1, physician's options step 2, graft selection step 3, and online order step 4. Aneurysm measurement step 1 is highlighted.

Figure 8:
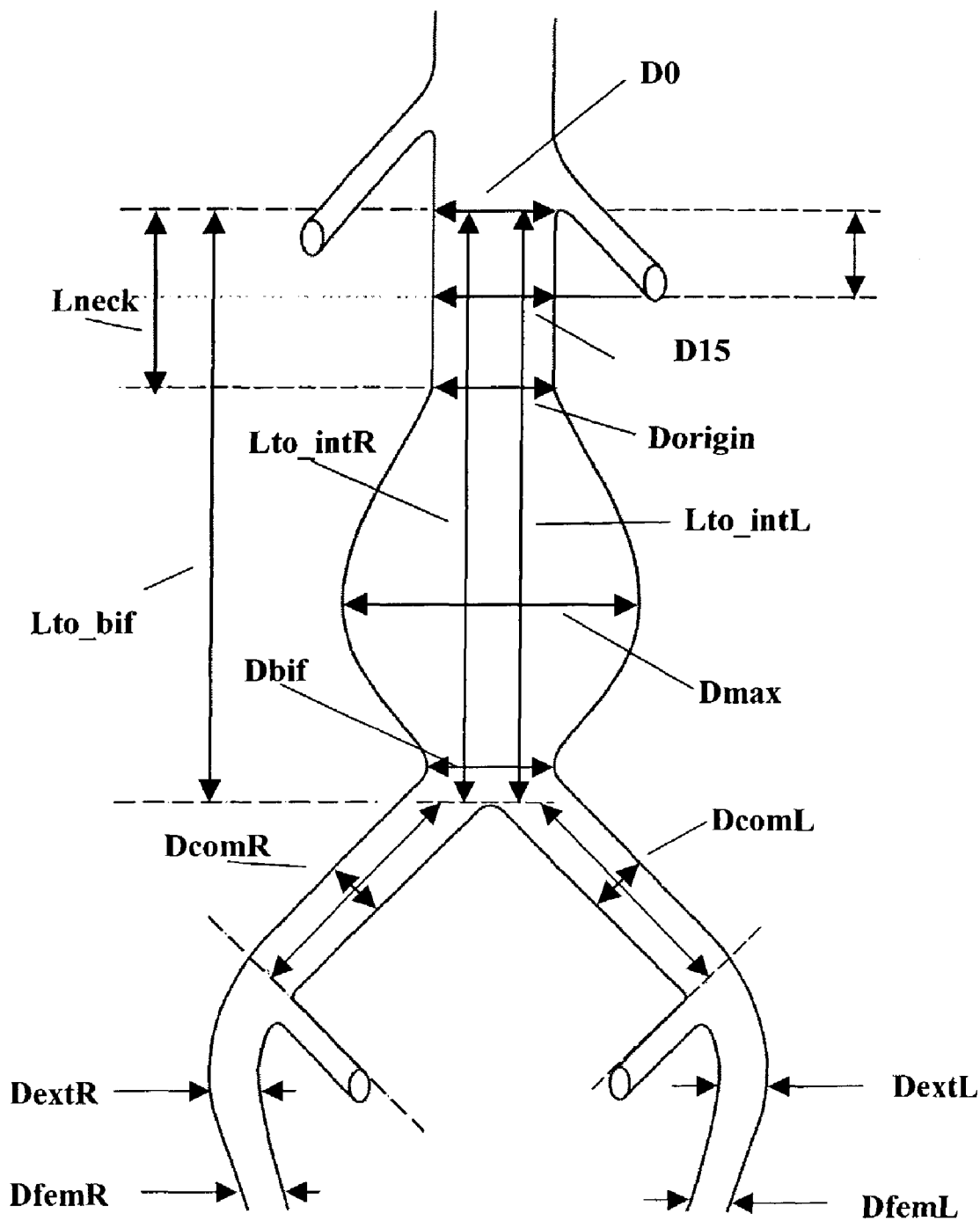
FIG. 8 is an example of an aortic aneurysm graphic and a definition of the various lengths and diameters used in characterizing the aneurysm and the vessels associated with the aneurysm.

Real-time graphic region 302A includes an illustration of an aortic aneurysm graphic 790 using default dimensions. FIG. 8 is an example of an aortic aneurysm and a definition of the various lengths and diameters used in characterizing the aneurysm and the vessels associated with the aneurysm. TABLE 1 presents a description of each reference numeral in FIG. 8 and a default size that is used to generate the initial 2D aortic aneurysm graphic 790 in real-time graphic region 302A.

TABLE 1

| Reference Numeral | Description | Default Size (mm) |
|---|---|---|
| Lneck | Proximal aortic neck length | 30 |
| Lto_bif | Lowest renal artery to aortic bifurcation length | 100 |
| Lto_intR | Lowest renal artery to right internal iliac artery | 140 |

TABLE 1-continued

| Reference Numeral | Description | Default Size (mm) |
|---|---|---|
| Lto_intL | Lowest renal artery to left internal iliac artery | 140 |
| D0 | Aorta diameter at lowest renal artery | 20 |
| D15 | Aorta diameter 15 mm below lowest renal artery | 20 |
| Dorigin | Aorta diameter at aneurysm origin | 20 |
| Dmax | Aneurysm maximum diameter | 50 |
| Dbif | Aorta diameter at bifurcation | 20 |
| DcomR | Right common iliac artery diameter | 10 |
| DcomL | Left common iliac artery diameter | 10 |
| DextR | Right external iliac artery diameter | 8 |
| DextL | Left external iliac artery diameter (smallest diameter) | 8 |
| DfemR | Right common femoral artery diameter | |
| DfemL | Left common femoral artery diameter | |

In one embodiment, FIG. 8 and TABLE 1 are presented in a help pop-up window for the user.

Continuing with the regions of aneurysm proximal neck graphic user interface 710, data entry progress indicator region 304A includes three indicators for the steps in this example of aneurysm measurement step 1, i.e., proximal neck step 1*a*, aneurysm step 1*b*, and iliac/femoral step 1*c*. Proximal neck step 1*a* indicator is highlighted to show the user that proximal neck step 1*a* in aneurysm measurement step 1 is being started.

A data input region 703 is a combination of pull-down menus 721, 722 data windows 731, 732, 733, 734, 735, 736, 737, 738, and check boxes 741, 742, 743, 744. A value for a lowest renal artery to be preserved is selected from a pull down menu 721. The options in pull down menu 721 are right main renal artery; left main renal artery; right accessory artery; and left accessory artery. Only one option can be selected.

A first data window 731 is used for entry of a length of a proximal aortic neck Lneck in millimeters. When the user places a cursor in first data window 731, the required dimension is illustrated on aortic aneurysm graphic 790 in real-time graphic region 302A using a dimension arrow and a reference numeral, as illustrated in FIG. 7. Also, the portion of aortic aneurysm graphic 790, for which a measurement is to be entered in window 731, is highlighted. Alternatively, only the highlighting or only the dimension arrow could be displayed on aortic aneurysm graphic 790. While it is not shown, when the user places the cursor in any of data windows 732 to 738, the corresponding reference numeral and arrow from FIG. 8 is presented on aortic aneurysm graphic 790 and the corresponding portion is highlighted in a manner similar to that for reference numeral Lneck.

The user enters a value in millimeters (mm), for length of proximal aortic neck Lneck, in first data window 731. The entered value is checked to determine whether the entered value is within a range of valid values for length of proximal aortic neck Lneck, for example, greater than zero mm and less than eighty mm. If the entered value is outside the range of valid values for the length, the user is asked to re-check the input.

If the entered value is in the valid range of values, but is less than a minimum permitted value of length of proximal aortic neck Lneck, e.g., 15 mm, for use of the stent-graft, a warning is presented to the user. For example, "A proximal neck length of at least 15 mm is recommended".

Figure 9:
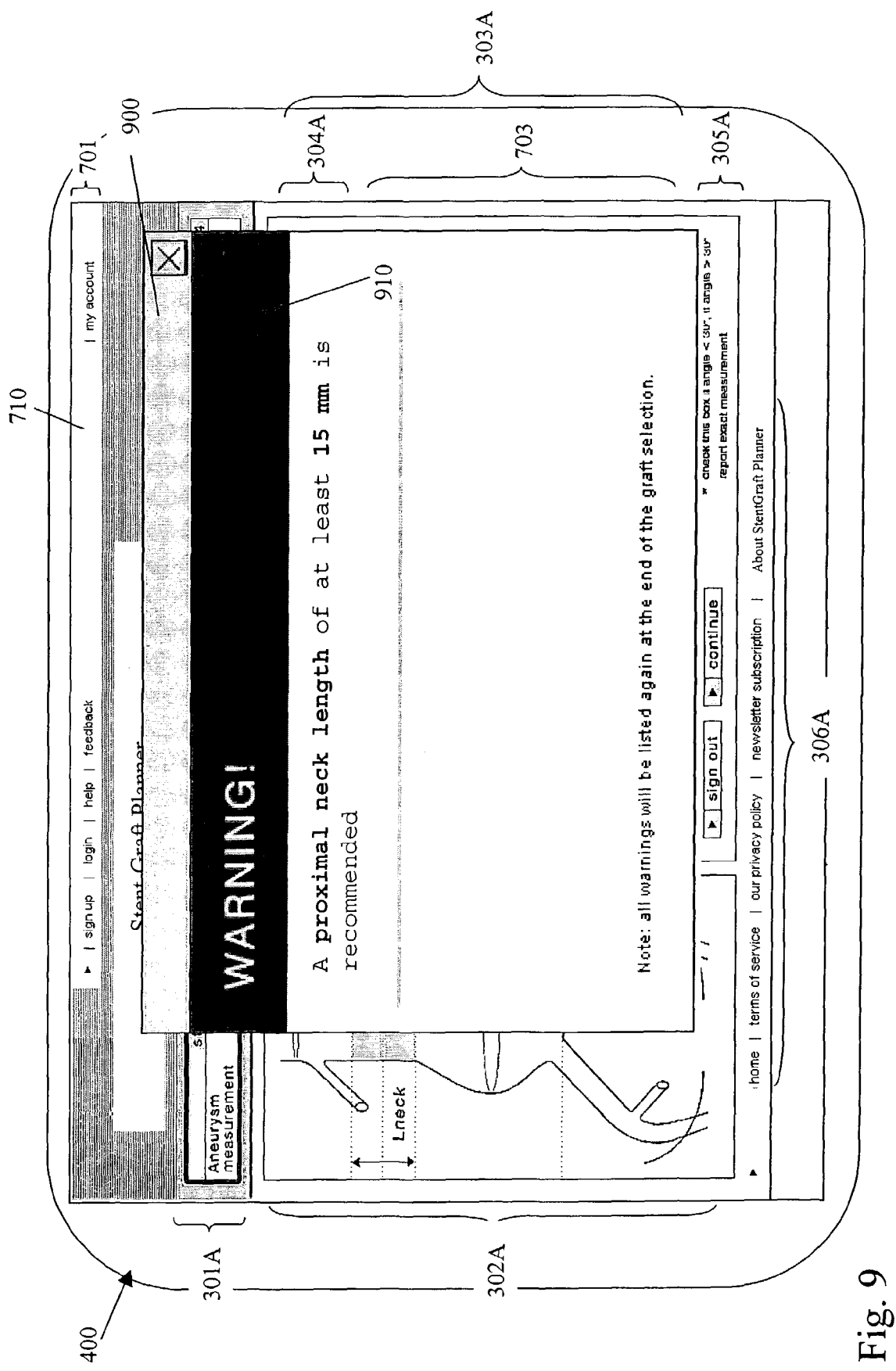
FIG. 9 is an example of a warning displayed in a pop-up window.

FIG. 9 is an example of a warning message 900 that is presented in a pop-up window. Typically, warning region 910 is bright red in color. In this example, each warning is saved, and when the graft selection is completed, the physician must acknowledge the set of warnings. In another example, a button and/or check box is included in warning message 900. To clear the message, the physician must either accept the warning, or click to clear the value that resulted in generation of the warning. Typically, at least some of the warnings are provided by a manufacturer. The manufacturer warnings are incorporated in stent-graft database 114.

Returning to FIG. 7, in one example, after a valid value is entered in window 731, aortic aneurysm graphic 790 is redrawn using that value and the redrawn portion is highlighted. This provides a visual representation that the physician can compare with the image being used to obtain the measurement.

A second data window 732 is for entry of a diameter of the aorta at the lowest renal artery D0 (FIG. 8) in millimeters. When the user places a cursor in second data window 732, dimension D0 is illustrated on aortic aneurysm graphic 790 in real-time graphic region 302A and the diameter is highlighted.

The user enters a value in millimeters (mm), for diameter of the aorta at the lowest renal artery D0 in second data window 732. The entered value is checked to determine whether the entered value is within a range of valid values for diameter of the aorta at the lowest renal artery D0, for example, greater than ten mm and less than forty mm. If the entered value is outside the range of valid diameter values, the user is asked to re-check the input.

If the value of the diameter is in the valid range of values, but is greater than or equal to a predefined value of diameter of the aorta diameter at the lowest renal artery D0, e.g., 28 mm, for use with stent graft, a warning is presented to the user. For example, "A diameter of less than 28 mm is recommended at the renal artery." After a valid value is entered in window 732, aortic aneurysm graphic 790 is redrawn using that value and aorta diameter at the lowest renal artery D0 is highlighted.

A third data window 733 is for entry of a diameter of the aorta at 15 mm below the lowest renal artery D15 (FIG. 8) in millimeters. When the user places a cursor in third data window 733, the required dimension D15 is illustrated on aortic aneurysm graphic 790 in real-time graphic region 302A with a dimension arrow as illustrated in FIG. 8 and diameter of the aorta at 15 mm below the lowest renal artery D15 also is highlighted.

The user enters a value in millimeters (mm), for diameter of the aorta at 15 mm below the lowest renal artery D15, in third data window 733. The entered value is checked to determine whether the entered value is within a range of valid values for diameter of the aorta at 15 mm below the lowest renal artery D15 in millimeters, for example, greater than ten mm and less than forty mm. If the entered value is outside the range of valid diameter values, the user is asked to re-check the input. After a valid value is entered in window 733, aortic aneurysm graphic 790 is redrawn using that value and diameter of the aorta at 15 mm below the lowest renal artery D15 is highlighted.

A fourth data window 734 is for entry of a diameter of the aorta at the aneurysm origin Dorigin (FIG. 8) in millimeters. When the user places a cursor in fourth data window 734, dimension Dorigin is illustrated on aortic aneurysm graphic 790 in real-time graphic region 302A via a dimension arrow as illustrated in FIG. 8, and diameter of the aorta at the aneurysm origin Dorigin also is highlighted.

The user enters a value in millimeters (mm), for diameter of the aorta at the aneurysm origin Dorigin in fourth data window 734. The entered value is checked to determine whether the entered value is within a range of valid values for diameter of the aorta at the aneurysm origin Dorigin, for example, greater than ten mm and less than forty mm. If the entered value is outside the range of valid diameter values, the user is asked to re-check the input.

If the value of the diameter is in the valid range of values, but diameter of the aorta at the aneurysm origin Dorigin minus diameter of the aorta diameter at the lowest renal artery D0 is greater than or equal to a predefined value, e.g., three mm, a warning is presented to the user. For example, "An inverted funnel shape of the proximal neck is present. Stent graft placement in this condition is not recommended." After a valid value is entered in window 734, aortic aneurysm graphic 790 is redrawn using that value.

Checkbox 741 is for a suprarenal antero-posterior angle $\alpha 1$ (FIGS. 10A and 10B) of less than 30°. A fifth data window 735 is for a suprarenal antero-posterior angle $\alpha 1$ of greater than or equal to 30°. Before considering check box 741 and data window 735, the definitions of the angles are considered.

Figure 10A:
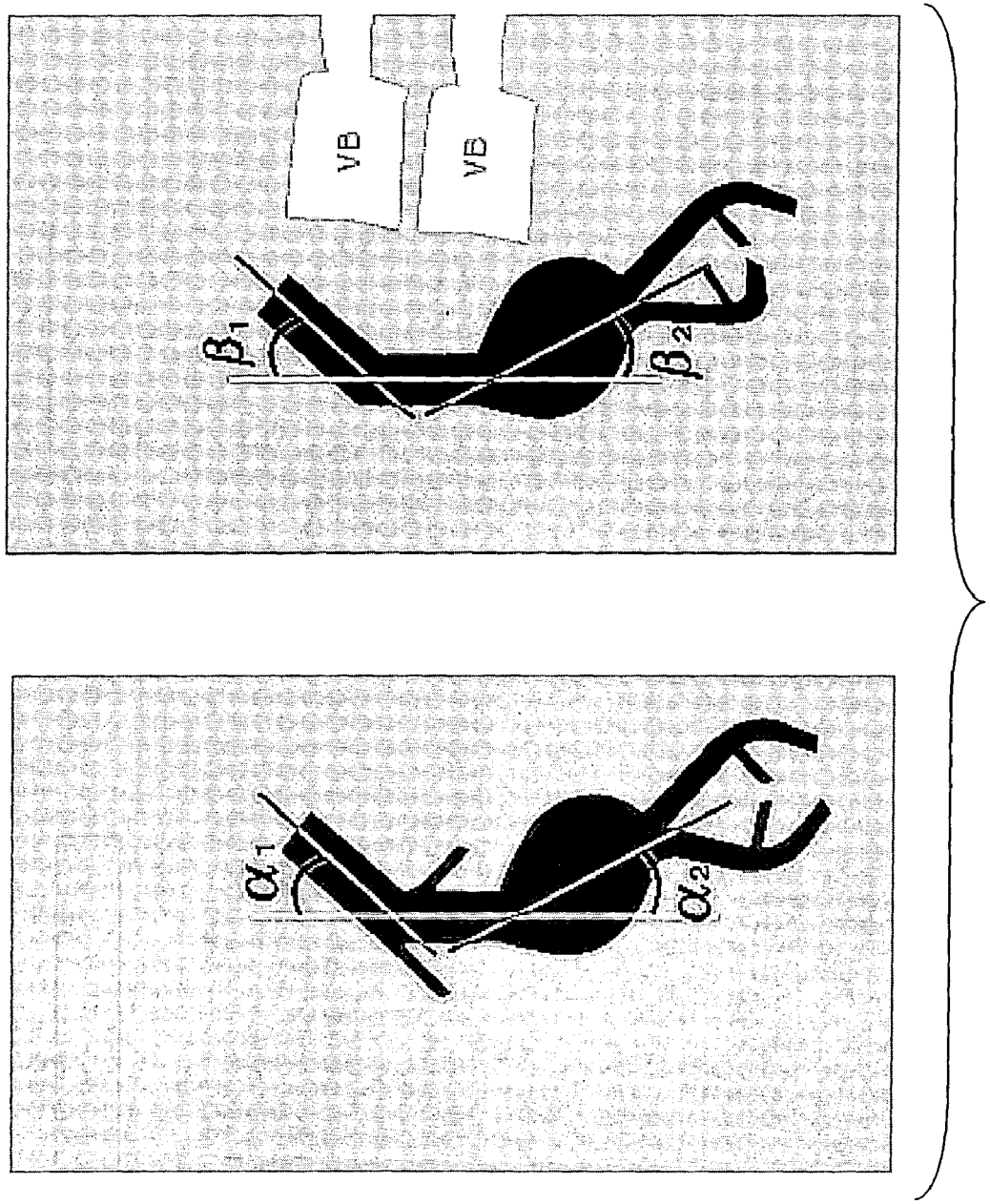
FIG. 10A is a first schema that shows how to measure suprarenal antero-posterior angle $\alpha 1$, suprarenal angle lateral $\beta 1$, neck-to-aneurysm angle antero-posterior $\alpha 2$, and neck-to-aneurysm angle lateral $\beta 2$.
Figure 10B:
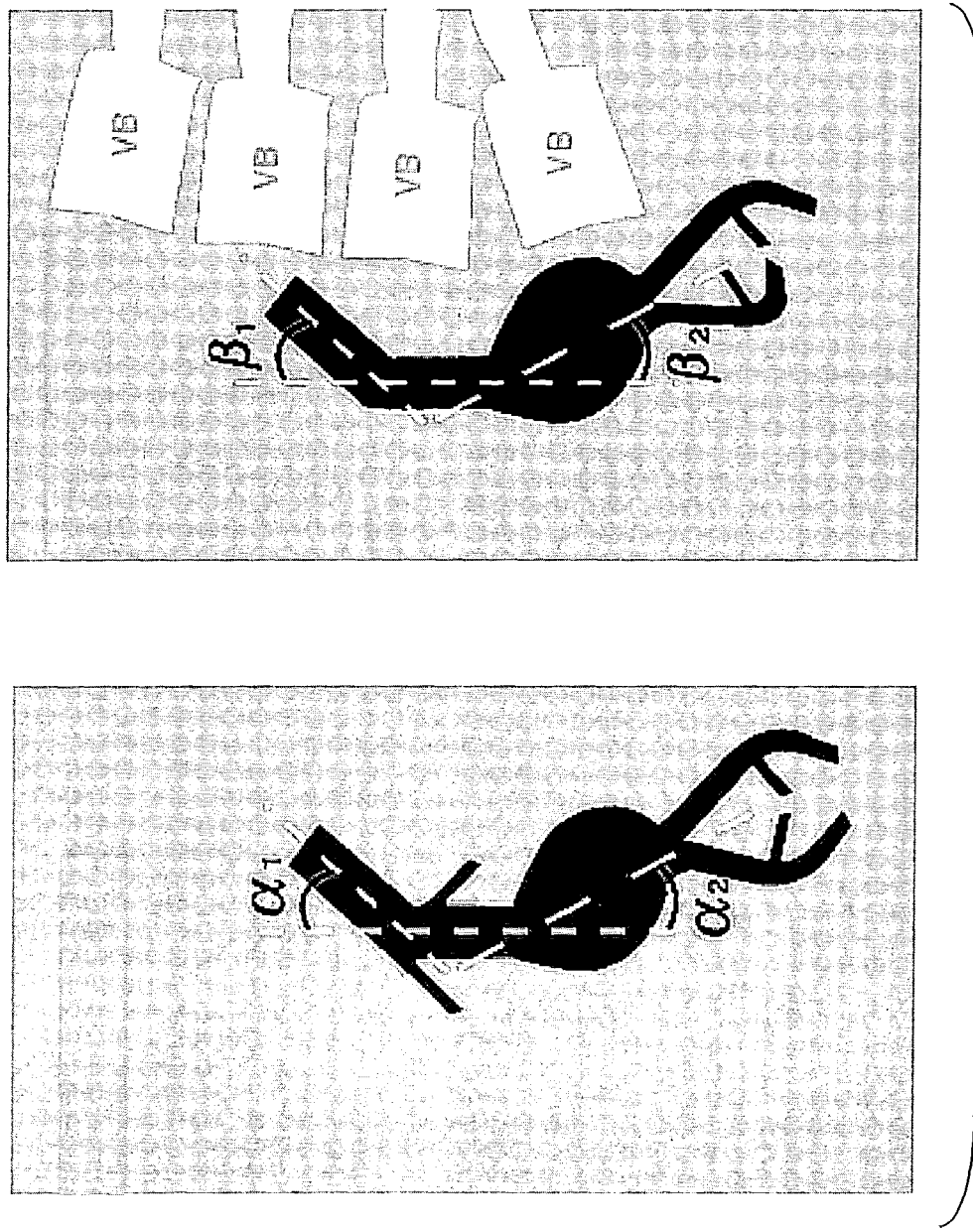
FIG. 10B is a second schema that shows how to measure suprarenal antero-posterior angle $\alpha 1$, suprarenal angle lateral $\beta 1$, neck-to-aneurysm angle antero-posterior $\alpha 2$, and neck-to-aneurysm angle lateral $\beta 2$.

FIG. 10A is a first schema that shows how to measure suprarenal antero-posterior angle $\alpha 1$, suprarenal angle lateral $\beta 1$, neck-to-aneurysm angle antero-posterior $\alpha 2$, and neck-to-aneurysm angle lateral $\beta 2$. FIG. 10B is a second schema that shows how to measure suprarenal antero-posterior angle $\alpha 1$, suprarenal angle lateral $\beta 1$, neck-to-aneurysm angle antero-posterior $\alpha 2$, and neck-to-aneurysm angle lateral $\beta 2$. FIGS. 10A and 10B are provided as help pop-up windows.

Returning to consideration of check box 741 and data window 735, if suprarenal antero-posterior angle $\alpha 1$ is less than 30°, the user checks check box 741 and otherwise enters a value in degrees in window 735. The value entered in window 735 is checked to determine whether the value is within a range of valid values for suprarenal antero-posterior angle $\alpha 1$, for example, greater than or equal to 30° and less than 180°. If the value entered is outside the range of valid values, the user is asked to re-check the input.

If the value of suprarenal antero-posterior angle $\alpha 1$ is in the valid range of values, but suprarenal antero-posterior angle $\alpha 1$ is greater than 60°, a warning is presented to the user. For example, "An angulation of more than 60° is present. Stent graft placement is not recommended in this condition."

Checkbox 742 is for suprarenal angle lateral $\beta 1$ (FIGS. 10A and 10B) of less than 30°. A sixth data window 736 is for a suprarenal angle lateral $\beta 1$ of greater than or equal to 30°. If suprarenal angle lateral $\beta 1$ is less than 30°, the user checks check box 742 and otherwise enters a value in degrees in window 736. The value entered in window 736 is checked to determine whether the value is within a range of valid values for suprarenal angle lateral $\beta 1$, for example, greater than or equal to 30° and less than 180°. If the value entered is outside the range of valid values, the user is asked to re-check the input.

If the value of suprarenal angle lateral $\beta 1$ is in the valid range of values, but suprarenal angle lateral $\beta 1$ is greater than 60°, or some other selected maximum value, a warning is presented to the user. For example, "An angulation of more than 60° is present. Stent graft placement is not recommended in this condition."

Checkbox 743 is for a neck-to-aneurysm angle antero-posterior $\alpha 2$ (FIGS. 10A and 10B) of less than 30°. A seventh data window 737 is for a neck-to-aneurysm angle antero-posterior $\alpha 2$ of greater than or equal to 30°. If neck-to-aneurysm angle antero-posterior $\alpha 2$ is less than 30°, the user checks check box 743 and otherwise enters a value in degrees in window 737. The value entered in window 737 is checked to determine whether the value is within a range of valid values for neck-to-aneurysm angle antero-posterior α2, for example, greater than or equal to 30° and less than 180°. If the value entered is outside the range of valid values, the user is asked to re-check the input.

If the value of neck-to-aneurysm angle antero-posterior α2 is in the valid range of values, but neck-to-aneurysm angle antero-posterior α2 is greater than 60°, or some other selected maximum value, a warning is presented to the user. For example, "An angulation of more than 60° is present. Stent graft placement is not recommended in this condition."

Checkbox 744 is for a neck-to-aneurysm angle lateral β2 (FIGS. 10A and 10B) of less than 30°. An eighth data window 738 is for a neck-to-aneurysm angle lateral β2 of greater than or equal to 30°. If neck-to-aneurysm angle lateral β2 is less than 30°, the user checks check box 744 and otherwise enters a value in degrees in window 738. The value entered in window 738 is checked to determine whether the value is within a range of valid values for neck-to-aneurysm angle lateral β2, for example, greater than or equal to 30° and less than 180°. If the value entered is outside the range of valid values, the user is asked to re-check the input.

If the value of neck-to-aneurysm angle lateral β2 is in the valid range of values, but neck-to-aneurysm angle lateral β2 is greater than 60°, or some other selected maximum value, a warning is presented to the user. For example, "An angulation of more than 60° is present. Stent graft placement is not recommended in this condition."

A value for a thrombus of the proximal neck is selected from a pull down menu 722. The options in pull down menu 721 are: 1, 2, 3, and 4. One is the default selection.

A pop-up help window is provided to help the user interpret the values in pull down menu 722. An example of the information in the pop-up help window is presented in TABLE 2.

TABLE 2

| Value in Thrombus Pull Down Menu 722 | Proximal Neck Thrombus Severity |
|---|---|
| 1 | No thrombus |
| 2 | Mild thrombus |
| 3 | Moderate thrombus |
| 4 | Severe thrombus (Circumferential thrombus of entire proximal neck) |

When a value is selected from thrombus pull down menu 722, the value is checked to determine whether the value is greater than or equal to a predefined value, for example, greater than or equal to three. If the value is greater than or equal to the predefined value, a warning is provided to the user. For example, "Severe thrombus is present. Stent-graft placement is not recommended in this condition."

After valid data has been entered for all of the items in aneurysm proximal neck graphic user interface 710, continue button 752 is activated in navigation region 305A. In this example, navigation region 305A includes a sign out button 751 and continue button 752. Sign out button 751 is always active.

If the user selects sign out button 751, a pop-up window appears and asks the user to confirm the sign out request or whether the user wants to select a new stent graft. If the user confirms the sign out request, all the data that has been entered and a reference to the current graphic user interface are saved in physician database 111 so that the session can be restarted later.

If the user selects continue button 752, the data entered on aneurysm proximal neck graphic user interface 710 is saved along with any warnings that were generated. Aneurysm graphic user interface 1110 (FIG. 11) is then displayed on screen 400 for aneurysm measurement step 1, 1b Aneurysm.

Figure 11:
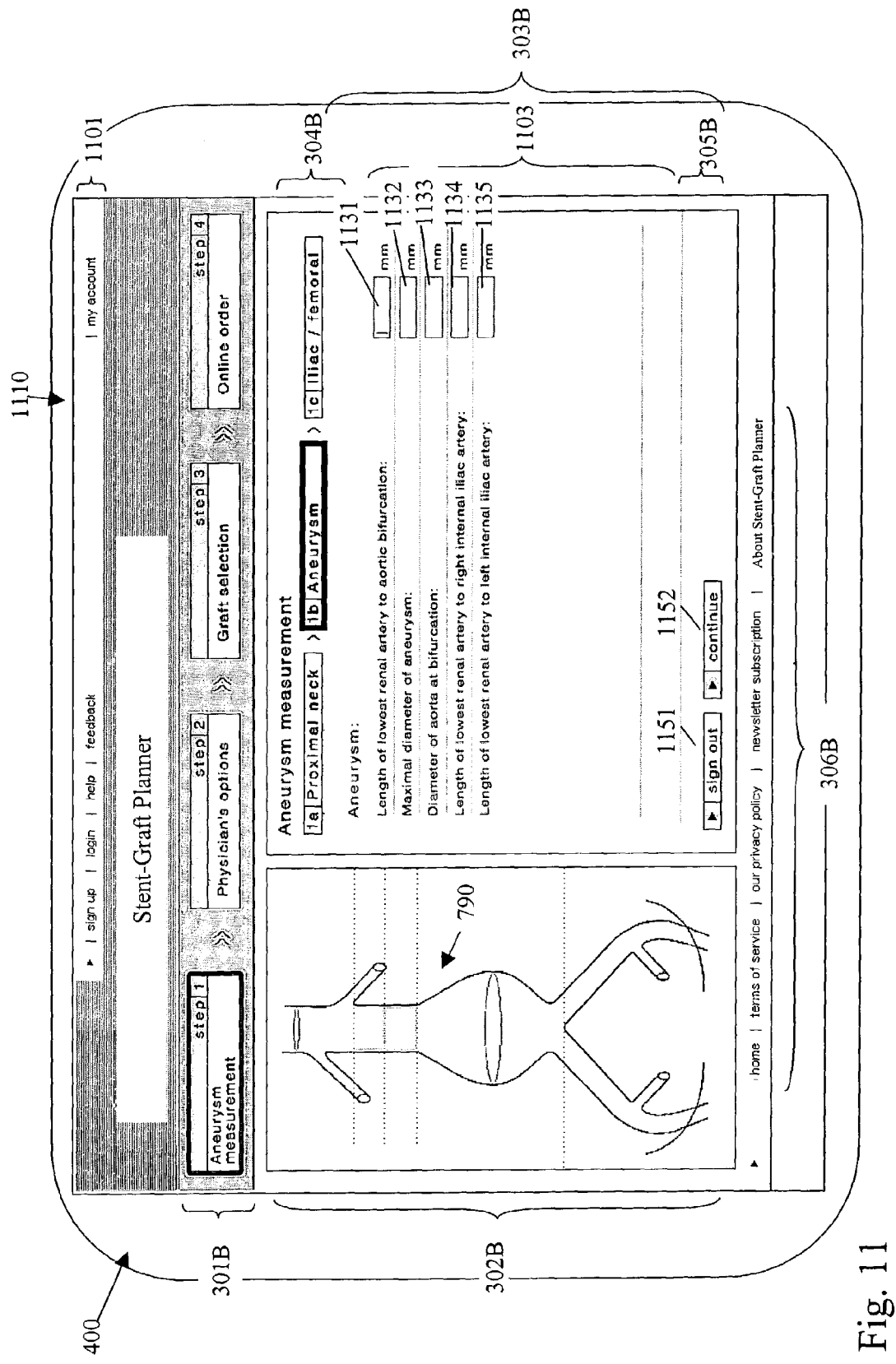
FIG. 11 is an example of an aneurysm graphic user interface displayed on a display device.

While it is not shown in FIG. 11, the aneurysm portion of aortic aneurysm graphic 790 is highlighted when aneurysm graphic user interface 1110 is first displayed.

Aneurysm graphic user interface 1110 includes each of the regions as described above for FIG. 3, i.e., regions 301B, 302B, 303B, 304B, 305B, 306B. In this example, other information options region 306B is the same as region 306A (FIG. 7) and that description is incorporated by reference herein. Another information options region 1101 includes links to sign up, login, help, feedback, and my account.

In stent-graft planning progress guide region 301B, four steps are again illustrated, aneurysm measurement step 1, physician's options step 2, graft selection step 3, and online order step 4. Aneurysm measurement step 1 is still highlighted.

Real-time graphic region 302B includes aortic aneurysm graphic 790 using the collected dimensions and the default dimensions for parameters for which dimensions have not yet been collected.

Data entry progress indicator region 304B includes three indicators for the steps in this example of aneurysm measurement step 1, i.e., proximal neck step 1a, aneurysm step 1b, and iliac/femoral step 1c. Aneurysm step 1b indicator is highlighted to show the user that aneurysm step 1b is being started.

A data input region 1103 includes data windows 1131, 1132, 1133, 1134, 1135. A first data window 1131 is used for entry of a length from a lowest renal artery to the aortic bifurcation Lto_bif (FIG. 8 and TABLE 1) in millimeters. When the user places a cursor in first data window 1131, the required dimension is illustrated on aortic aneurysm graphic 790 in real-time graphic region 302B using a dimension arrow and a reference numeral. Also, the portion of aortic aneurysm graphic 790, for which a measurement is to be entered in window 1131, is highlighted. Alternatively, only the highlighting or only the dimension arrow could be displayed on aortic aneurysm graphic 790. While it is not shown, when the user places the cursor in any of data windows 1132 to 1135, the corresponding reference numeral and arrow from FIG. 8 is presented on aortic aneurysm graphic 790 and the corresponding portion is highlighted.

The user enters a value in millimeters (mm), for a lowest renal artery to the aortic bifurcation length Lto_bif, in first data window 1131. The entered value is checked to determine whether the entered value is within a range of valid values for length from lowest renal artery to the aortic bifurcation Lto_bif, for example, greater than fifty mm and less than two hundred mm. If the entered value is outside the range of valid values for the length, the user is asked to re-check the input.

If the value is in the valid range of values, but is less than a permitted minimum value of length from a lowest renal artery to the aortic bifurcation Lto_bif for use of the stent-graft, e.g., 80 mm, or greater than a permitted maximum value of length from a lowest renal artery to the aortic bifurcation Lto_bif for use of the stent-graft, e.g., 155 mm, a warning is presented to the user. For example, "A stent-graft placement is not recommended in this patient. The distance from length from the lowest renal artery to the aortic bifurcation has to be between 80 and 155 mm." See FIG. 9 for an example of a warning.

After a valid value is entered in window 1131, aortic aneurysm graphic 790 is redrawn using that value and the redrawn portion is highlighted. This provides a visual representation that the physician can compare with the image being used to obtain the measurement.

A second data window 1132 is for entry of a maximum diameter of the aneurysm Dmax (FIG. 8) in millimeters. When the user places a cursor in second data window 1132, dimension Dmax is illustrated on aortic aneurysm graphic 790 in real-time graphic region 302B and the diameter is highlighted.

The user enters a value in millimeters (mm), for maximum diameter of the aneurysm Dmax in second data window 1132. The entered value is checked to determine whether the entered value is within a range of valid values for maximal diameter of the aneurysm Dmax, for example, greater than 30 mm and less than 150 mm. If the entered value is outside the range of valid diameter values, the user is asked to re-check the input. After a valid value is entered in window 1132, aortic aneurysm graphic 790 is redrawn using that value and maximum diameter of the aneurysm Dmax is highlighted.

A third data window 1133 is for entry of a diameter of the aorta at bifurcation Dbif (FIG. 8) in millimeters. When the user places a cursor in third data window 1133, the required dimension Dbif is illustrated on aortic aneurysm graphic 790 in real-time graphic region 302B and diameter of the aorta at bifurcation Dbif is highlighted.

The user enters a value in millimeters (mm), for diameter of the aorta at bifurcation Dbif, in third data window 1133. The entered value is checked to determine whether the entered value is within a range of valid values for diameter of the aorta at bifurcation Dbif in millimeters, for example, greater than zero mm and less than 150 mm. If the entered value is outside the range of valid diameter values, the user is asked to re-check the input.

If the value of the diameter is in the valid range of values, but is less than a first predefined value of diameter of the aorta at bifurcation Dbif, e.g., twenty mm, for use with stent graft, a first warning is presented to the user. For example, "Post-deployment kissing angioplasty should be considered for appropriate limb expansion."

If the value of the diameter is in the valid range of values, but is less than a second predefined value of diameter of the aorta at bifurcation Dbif, e.g., twelve mm, for use with stent graft, a second warning is presented to the user. For example, "Prohibitive anatomy—Appropriate stent graft placement may not be possible."

After a valid value is entered in window 1133, aortic aneurysm graphic 790 is redrawn using that value and diameter of the aorta at bifurcation Dbif is highlighted.

A fourth data window 1134 is used for entry of a length from a lowest renal artery to the right internal iliac artery Lto_intR (FIG. 8 and TABLE 1) in millimeters. When the user places a cursor in fourth data window 1134, the required dimension is illustrated on aortic aneurysm graphic 790 in real-time graphic region 302B using two dimension arrows (See FIG. 8) and a reference numeral. Also, the portion of aortic aneurysm graphic 790, for which a measurement is to be entered in window 1134, is highlighted.

Alternatively, only the highlighting or only the dimension arrows could be displayed on aortic aneurysm graphic 790.

The user enters a value in millimeters (mm), for a length from a lowest renal artery to the right internal iliac artery Lto_intR, in fourth data window 1134. The entered value is checked to determine whether the entered value is within a range of valid values for length from a lowest renal artery to the right internal iliac artery Lto_intR, for example, greater than eighty mm and less than 250 mm. If the entered value is outside the range of valid values for the length, the user is asked to re-check the input. After a valid value is entered in window 1134, aortic aneurysm graphic 790 is redrawn using that value and the redrawn portion is highlighted. This provides a visual representation that the physician can compare with the image being used to obtain the measurement.

A fifth data window 1135 is used for entry of a length from a lowest renal artery to the left internal iliac artery Lto_intL (FIG. 8 and TABLE 1) in millimeters. When the user places a cursor in fifth data window 1135, the required dimension is illustrated on aortic aneurysm graphic 790 in real-time graphic region 302B using two dimension arrows (See FIG. 8) and a reference numeral. Also, the portion of aortic aneurysm graphic 790, for which a measurement is to be entered in window 1135, is highlighted. Alternatively, only the highlighting or only the dimension arrows could be displayed on aortic aneurysm graphic 790.

The user enters a value in millimeters (mm), for a length from a lowest renal artery to the left internal iliac artery Lto_intL, in fifth data window 1135. The entered value is checked to determine whether the entered value is within a range of valid values for length from a lowest renal artery to the left internal iliac artery Lto_intL, for example, greater than eighty mm and less than 250 mm. If the entered value is outside the range of valid values for the length, the user is asked to re-check the input. After a valid value is entered in window 1135, aortic aneurysm graphic 790 is redrawn using that value and the redrawn portion is highlighted. This provides a visual representation that the physician can compare with the image being used to obtain the measurement.

After valid data has been entered for all of the items in aneurysm graphic user interface 1110, continue button 1152 is activated in navigation region 305B. In this example, navigation region 305B includes a sign out button 1151 and continue button 1152. Sign out button 1151 is always active.

If the user selects sign out button 1151, a pop-up window appears and asks the user to confirm the sign out request or whether the user wants to select a new stent graft. If the user confirms the sign out request, all the data that has been entered and a reference to the current graphic user interface are saved in physician database 111 so that the session can be restarted later.

Figure 12:
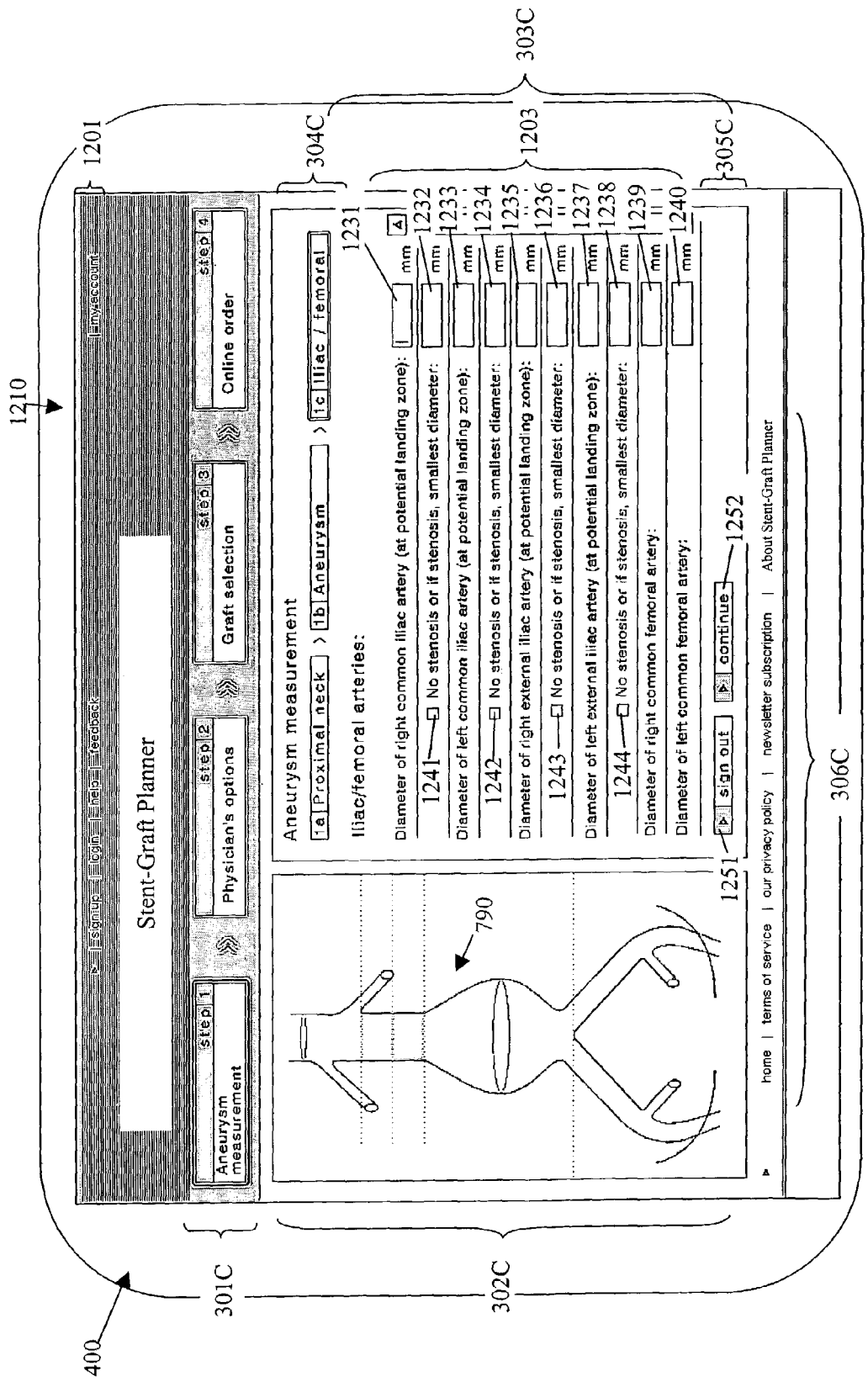
FIG. 12 is an example of an iliac/femoral graphic user interface displayed on a display device.

If the user selects continue button 1152, the data entered on aneurysm graphic user interface 1110 is saved along with any warnings that were generated in database 111. Iliac/femoral graphic user interface 1210 (FIG. 12) is then displayed on screen 400 for aneurysm measurement step 1, 1c iliac/femoral. While it is not shown in FIG. 12, the iliac/femoral portion of aortic aneurysm graphic 790 is highlighted when aneurysm graphic user interface 1210 is first displayed.

Iliac/femoral graphic user interface 1210 includes each of the regions as described above for FIG. 3, i.e., regions 301C, 302C, 303C, 304C, 305C, 306C. In this example, other information options region 306C is the same as region 306A (FIG. 7) and that description is incorporated by reference herein. Another information options region 1201 includes links to sign up, login, help, feedback, and my account.

In stent-graft planning progress guide region 301C, four steps are again illustrated, aneurysm measurement step 1, physician's options step 2, graft selection step 3, and online order step 4. Aneurysm measurement step 1 is still highlighted.

Real-time graphic region 302C includes aortic aneurysm graphic 790 using the collected dimensions and the default dimensions for parameters for which dimensions have not yet been collected.

Data entry progress indicator region 304C includes three indicators for the steps in this example of aneurysm measurement step 1, i.e., proximal neck step 1a, aneurysm step 1b, and iliac/femoral step 1c. Iliac/femoral step 1c indicator is highlighted to show the user that iliac/femoral step 1c is being started.

A data input region 1203 includes ten data windows 1231 to 1240 and four check boxes 1241 to 1244. A first data window 1231 is for entry of a diameter of the right common iliac artery DcomR (FIG. 8 and TABLE 1) in millimeters. When the user places a cursor in first data window 1241, the required dimension DcomR is illustrated on aortic aneurysm graphic 790 with a dimension arrow and reference numeral in real-time graphic region 302C and diameter of the right common iliac artery DcomR is highlighted.

The user enters a value in millimeters (mm), for diameter of the right common iliac artery DcomR, in first data window 1231. The entered value is checked to determine whether the entered value is within a range of valid values for diameter of the right common iliac artery DcomR in millimeters, for example, greater than zero mm and less than 120 mm. If the entered value is outside the range of valid diameter values, the user is asked to re-check the input.

If the value of the diameter is in the valid range of values, but is greater than a predefined value of diameter of the right common iliac artery DcomR, e.g., twenty mm, for use with stent graft, a warning is presented to the user. For example, "Vessel too large for distal fixation. Stent-graft placement in this condition is not recommended." After a valid value is entered in window 1231, aortic aneurysm graphic 790 is redrawn using that value and diameter of the right common iliac artery DcomR is highlighted.

Checkbox 1241 is for no stenosis in the right common iliac artery. A second data window 1232 is for entry of a smallest diameter of the right common iliac artery DcomRsmall. If the user checks check box 1241, no further processing is done, and processing continues with third window 1233.

Alternatively, the user enters a value in millimeters (mm), for smallest diameter of the right common iliac artery DcomRsmall, in second data window 1232. The entered value is checked to determine whether the entered value is within a range of valid values for smallest diameter of the right common iliac artery DcomRsmall in millimeters, for example, greater than zero mm and less than 20 mm. If the entered value is outside the range of valid diameter values, the user is asked to re-check the input.

If the value of smallest diameter of the right common iliac artery DcomRsmall is in the valid range of values, but smallest diameter of the right common iliac artery DcomRsmall or diameter of right common iliac artery DcomR is less than a predefined value, e.g., 7.5 mm, for use of the stent graft, a warning is presented to the user. For example, "Small vessel for delivery system. Stent-graft placement in this condition is not recommended." After a valid value is entered in window 1232, aortic aneurysm graphic 790 is redrawn using that value showing the narrowed right common iliac artery.

A third data window 1233 is for entry of a diameter of the left common iliac artery DcomL (FIG. 8 and TABLE 1) in millimeters. When the user places a cursor in third data window 1233, the required dimension DcomL is illustrated on aortic aneurysm graphic 790 with a dimension arrow and reference numeral in real-time graphic region 302C and diameter of left common iliac artery DcomL is highlighted.

The user enters a value in millimeters (mm), for diameter of the left common iliac artery DcomL, in third data window 1233. The entered value is checked to determine whether the entered value is within a range of valid values for diameter of left common iliac artery DcomL in millimeters, for example, greater than zero mm and less than 120 mm. If the entered value is outside the range of valid diameter values, the user is asked to re-check the input.

If the value of the diameter is in the valid range of values, but is greater than a predefined value of diameter of the left common iliac artery DcomL, e.g., twenty mm, for use with stent graft, a warning is presented to the user. For example, "Vessel too large for distal fixation. Stent-graft placement in this condition is not recommended." After a valid value is entered in window 1233, aortic aneurysm graphic 790 is redrawn using that value and diameter of left common iliac artery DcomL is highlighted.

Checkbox 1242 is for no stenosis in the left common iliac artery. A fourth data window 1234 is for entry of a smallest diameter of the left common iliac artery DcomLsmall. If the user checks check box 1242, no further processing is done, and processing continues with fifth data window 1235.

Alternatively, the user enters a value in millimeters (mm), for smallest diameter of the left common iliac artery DcomLsmall, in fourth data window 1234. The entered value is checked to determine whether the entered value is within a range of valid values for smallest diameter of the left common iliac artery DcomLsmall in millimeters, for example, greater than zero mm and less than 20 mm. If the entered value is outside the range of valid diameter values, the user is asked to re-check the input.

If the value of smallest diameter of the left common iliac artery DcomLsmall is in the valid range of values, but smallest diameter of left common iliac artery DcomLsmall or diameter of left common iliac artery DcomL is less than a predefined value, e.g., 7.5 mm, for use of the stent graft, a warning is presented to the user. For example, "Small vessel for delivery system. Stent-graft placement in this condition is not recommended." After a valid value is entered in window 1234, aortic aneurysm graphic 790 is redrawn using that value and showing the narrowed left common iliac artery.

A fifth data window 1235 is for entry of a diameter of the right external iliac artery DextR (FIG. 8 and TABLE 1) in millimeters. When the user places a cursor in fifth data window 1235, the required dimension DextR is illustrated on aortic aneurysm graphic 790 with a dimension arrow and reference numeral in real-time graphic region 302C and diameter of the right external iliac artery DextR is highlighted.

The user enters a value in millimeters (mm), for diameter of the right external iliac artery DextR, in fifth data window 1235. The entered value is checked to determine whether the entered value is within a range of valid values for diameter of the right external iliac artery DextR in millimeters, for example, greater than zero mm and less than 50 mm. If the entered value is outside the range of valid diameter values, the user is asked to re-check the input.

If the value of the diameter is in the valid range of values, but is greater than a predefined value of diameter of the right external iliac artery DextR, e.g., twenty mm, for use with stent graft, a warning is presented to the user. For example, "Vessel too large for distal fixation. Stent-graft placement in this condition is not recommended." After a valid value is entered in window 1235, aortic aneurysm graphic 790 is redrawn using that value and diameter of the right external iliac artery DextR is highlighted.

Checkbox 1243 is for no stenosis in the right external iliac artery. A sixth data window 1236 is for entry of a smallest diameter of the right external iliac artery DextRsmall. If the user checks check box 1243, no further processing is done, and processing continues with seventh data window 1237.

Alternatively, the user enters a value in millimeters (mm), for smallest diameter of the right external iliac artery DextRsmall, in sixth data window 1236. The entered value is checked to determine whether the entered value is within a range of valid values for smallest diameter of the right external iliac artery DextRsmall in millimeters, for example, greater than zero mm and less than 20 mm. If the entered value is outside the range of valid diameter values, the user is asked to re-check the input.

If the entered value of smallest diameter of the right external iliac artery DextRsmall is in the valid range of values, but smallest diameter of the right external iliac artery DextRsmall or diameter of right external iliac artery DextR is less than a predefined value, e.g., 7.5 mm, for use of the stent graft, a warning is presented to the user. For example, "Small vessel for delivery system. Stent-graft placement in this condition is not recommended." After a valid value is entered in window 1236, aortic aneurysm graphic 790 is redrawn using that value showing the narrowed right external iliac artery.

A seventh data window 1237 is for entry of a diameter of the left external iliac artery DextL (FIG. 8 and TABLE 1) in millimeters. When the user places a cursor in seventh data window 1237, the required dimension DextL is illustrated on aortic aneurysm graphic 790 with a dimension arrow and reference numeral in real-time graphic region 302C and diameter of left external iliac artery DextL is highlighted.

The user enters a value in millimeters (mm), for diameter of the left external iliac artery DextL, in seventh data window 1237. The entered value is checked to determine whether the entered value is within a range of valid values for diameter of left external iliac artery DextL in millimeters, for example, greater than zero mm and less than 50 mm. If the entered value is outside the range of valid diameter values, the user is asked to re-check the input.

If the entered value of the diameter is in the valid range of values, but is greater than a predefined value of diameter of the left external iliac artery DextL, e.g., twenty mm, for use with stent graft, a warning is presented to the user. For example, "Vessel too large for distal fixation. Stent-graft placement in this condition is not recommended." After a valid value is entered in window 1237, aortic aneurysm graphic 790 is redrawn using that value and diameter of left external iliac artery DextL is highlighted.

Checkbox 1244 is for no stenosis in the left external iliac artery. An eighth data window 1238 is for entry of a smallest diameter of the left external iliac artery DextLsmall. If the user checks check box 1244, no further processing is done, and processing continues with ninth data window 1239.

Alternatively, the user enters a value in millimeters (mm), for smallest diameter of the left external iliac artery DextLsmall, in eighth data window 1238. The entered value is checked to determine whether the entered value is within a range of valid values for smallest diameter of the left external iliac artery DextLsmall in millimeters, for example, greater than zero mm and less than 20 mm. If the entered value is outside the range of valid diameter values, the user is asked to re-check the input.

If the value of smallest diameter of the left external iliac artery DextLsmall is in the valid range of values, but smallest diameter of left external iliac artery DextLsmall or diameter of left external iliac artery DextL is less than a predefined value, e.g., 7.5 mm, for use of the stent graft, a warning is presented to the user. For example, "Small vessel for delivery system. Stent-graft placement in this condition is not recommended." After a valid value is entered in window 1238, aortic aneurysm graphic 790 is redrawn using that value and showing the narrowed left external iliac artery.

A ninth data window 1239 is for entry of a diameter of the right common femoral artery DfemR (FIG. 8 and TABLE 1) in millimeters. When the user places a cursor in ninth data window 1239, the required dimension DfemR is illustrated on aortic aneurysm graphic 790 with a dimension arrow and reference numeral in real-time graphic region 302C and diameter of the right common femoral artery DfemR is highlighted.

The user enters a value in millimeters (mm), for diameter of the right common femoral artery DfemR, in ninth data window 1239. The entered value is checked to determine whether the entered value is within a range of valid values for diameter of the right common femoral artery DfemR in millimeters, for example, greater than zero mm and less than 20 mm. If the entered value is outside the range of valid diameter values, the user is asked to re-check the input.

If the value of the diameter is in the valid range of values, but is less than a predefined value of diameter of the right common femoral artery DfemR, e.g., 7.5 mm, for use with stent graft, a warning is presented to the user. For example, "Small vessel for delivery system. Stent-graft placement in this condition is not recommended." After a valid value is entered in window 1239, aortic aneurysm graphic 790 is redrawn using that value and diameter of the right common femoral artery DfemR is highlighted.

A tenth data window 1240 is for entry of a diameter of the left common femoral artery DfemL (FIG. 8 and TABLE 1) in millimeters. When the user places a cursor in tenth data window 1240, the required dimension DfemL is illustrated on aortic aneurysm graphic 790 with a dimension arrow and reference numeral in real-time graphic region 302C and diameter of left common femoral artery DfemL is highlighted.

The user enters a value in millimeters (mm), for diameter of the left common femoral artery DfemL, in tenth data window 1240. The entered value is checked to determine whether the entered value is within a range of valid values for diameter of left common femoral artery DfemL in millimeters, for example, greater than zero mm and less than 20 mm. If the entered value is outside the range of valid diameter values, the user is asked to re-check the input.

If the entered value of the diameter is in the valid range of values, but is less than a predefined value of diameter of the left common femoral artery DfemL, e.g., 7.5 mm, for use with stent graft, a warning is presented to the user. For example, "Small vessel for delivery system. Stent-graft placement in this condition is not recommended." After a valid value is entered in window 1240, aortic aneurysm graphic 790 is redrawn using that value and diameter of left common femoral artery DfemL is highlighted.

After valid data has been entered for all of the items in iliac/femoral graphic user interface 1210, continue button 1252, in this example, is activated in navigation region 305C. In this example, navigation region 305C includes a sign out button 1251 and continue button 1252. Sign out button 1251 is always active. Alternatively, continue button 1252 may also be always active.

If the user selects sign out button 1251, a pop-up window appears and asks the user to confirm the sign out request or whether the user wants to select a new stent graft. If the user confirms the sign out request, all the data that has been entered and a reference to the current graphic user interface are saved in physician database 111 so that the session can be restarted later.

Figure 13:
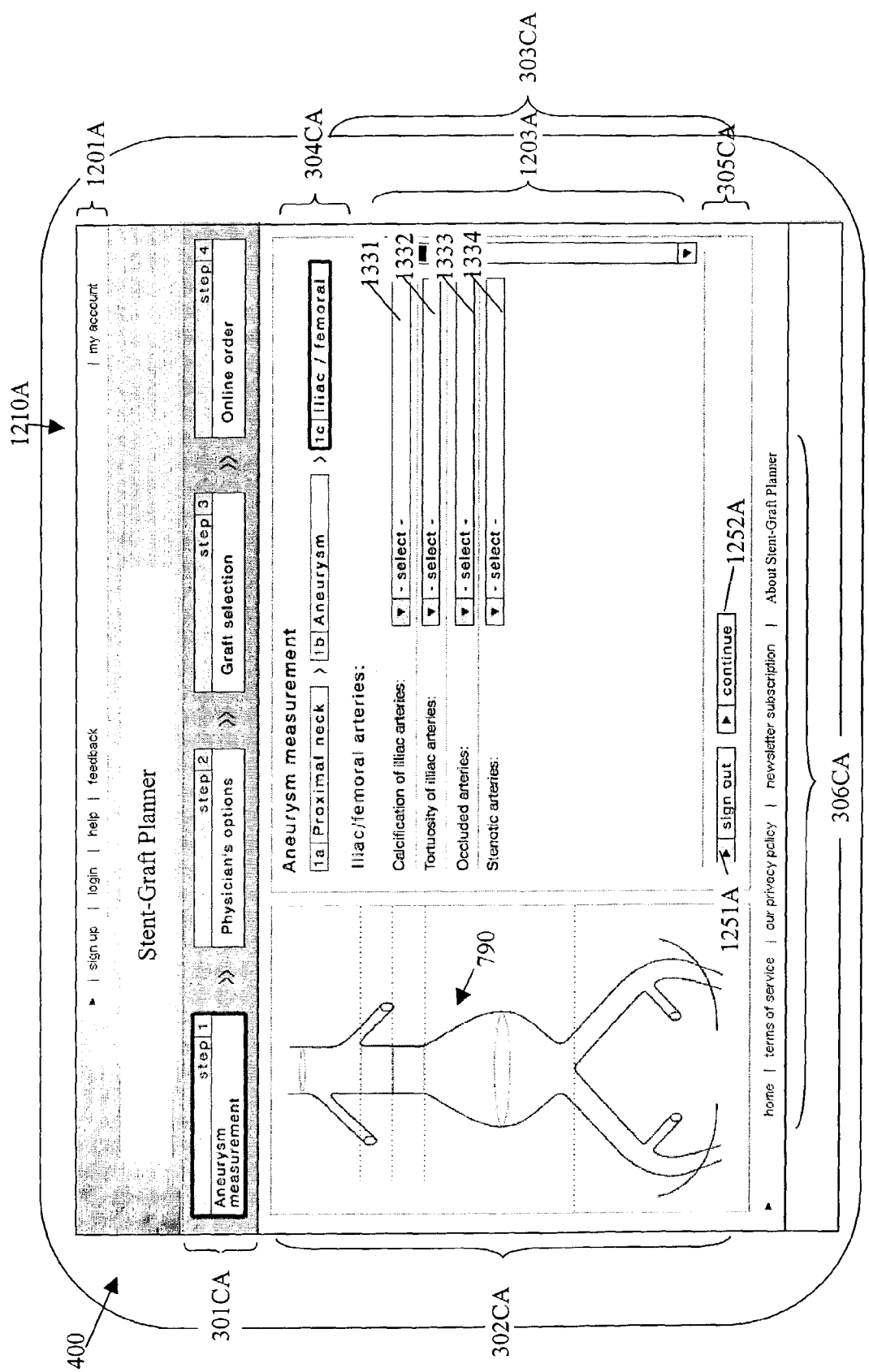
FIG. 13 is an example of a continued iliac/femoral graphic user interface displayed on a display device.

If the user selects continue button 1252, the data entered on iliac/femoral graphic user interface 1210 is saved along with any warnings that were generated. A continuation of iliac/ femoral graphic user interface 1210A (FIG. 13) is then displayed on screen 400 for aneurysm measurement step, 1c iliac/femoral. While it is not shown in FIG. 13, the iliac/femoral portion of aortic aneurysm graphic 790 is highlighted when continuation of iliac/femoral graphic user interface 1210A is first displayed.

Continuation of iliac/femoral graphic user interface 1210A includes each of the regions as described above for FIG. 12, i.e., regions 301CA, 302CA, 304CA, 305CA, 306CA, 1201A, which are equivalent to 301C, 302C, 304C, 305C, 306C, 1201, respectively, and the description of each is incorporated herein by reference.

A data input region 1203A includes four pull down menus 1331, 1332, 1333, 1334. A value for calcification of the iliac arteries is selected from a pull down menu 1331. The options in pull down menu 1331 are: 1, 2, 3, and 4. One is the default selection.

A pop-up help window is provided to help the user interpret the values in pull down menu 1331. An example of the information in the pop-up help window is presented in TABLE 3.

TABLE 3

| Value in Iliac Arteries Calcification Pull Down Menu | Iliac Arteries Calcification Severity |
|---|---|
| 1 | No calcification |
| 2 | Mild calcification |
| 3 | Moderate calcification |
| 4 | Severe calcification (Circumferential calcification of entire vessel length) |

When a value is selected from pull down menu 1331, the value is checked to determine whether the value is greater than or equal to a predefined value, for example, greater than or equal to three. If the value is greater than or equal to the predefined value, a warning is provided to the user. For example, "Severe calcification is present. Appropriate stent-graft placement may not be possible."

A value for tortuosity of the iliac arteries is selected from a pull down menu 1332. The options in pull down menu 1332 are: 1, 2, 3, and 4. One is the default selection.

A pop-up help window is provided to help the user interpret the values in pull down menu 1332. An example of the information in the pop-up help window is presented in TABLE 4.

TABLE 4

| Value in Iliac Arteries Tortuosity Pull Down Menu | Iliac Arteries Tortuosity Severity |
|---|---|
| 1 | No tortuosity |
| 2 | Mild tortuosity |
| 3 | Moderate tortuosity |
| 4 | Severe tortuosity (360° loop in any segment of the vessel) |

When a value is selected from pull down menu 1332, the value is checked to determine whether the value is greater than or equal to a predefined value, for example, greater than or equal to three. If the value is greater than or equal to the predefined value, a warning is provided to the user. For example, "Prohibited anatomy. Stent-graft placement is not recommended."

Occluded arteries are identified using pull down menu 1333. The options in pull down menu 1333 are: none, SMA, right internal iliac artery, and left internal artery, where SMA is superior mesenteric artery. None is the default selection. The user can make multiple selections in pull down menu 1333. After the user makes the selection or selections from pull down menu 1333, aortic aneurysm graphic 790 in real-time graphic region 302CA is redrawn with the occluded arteries illustrated in black.

When a value or values are selected from pull down menu 1333, the values are checked to determine whether both internal iliac arteries were selected. If both internal iliac arteries were selected, a warning is provided to the user. For example, "Occlusion of IMA (inferior mesenteric artery) during stent-graft placement may cause mesenteric ischemia when both internal iliac arteries are occluded. Stent-graft placement is not recommended in this condition."

The value or values selected from pull down menu 1333 are also checked to determine whether SMA was selected. If SMA was selected, a warning is provided to the user. For example, "Occlusion of IMA (inferior mesenteric artery) during stent-graft placement may cause mesenteric ischemia when SMA occlusion is present. Stent-graft placement is not recommended in this condition."

Stenotic arteries (greater than 50%, for example) are identified using pull down menu 1334. The options in pull down menu 1334 are: none, SMA, right internal iliac artery, and left internal artery. None is the default selection. The user can make multiple selections in pull down menu 1334. After the user makes the selection or selections from pull down menu 1334, aortic aneurysm graphic 790 in real-time graphic region 302CA is redrawn with the stenotic arteries shaded.

When a value or values are selected from pull down menu 1334, the values are checked to determine whether SMA was selected. If SMA was selected, a warning is provided to the user. For example, "Occlusion of IMA during stent-graft placement may cause mesenteric ischemia when SMA occlusion is present. Stent-graft placement is not recommended in this condition."

When the user selects continue button 1252A, the data is saved. This completes aneurysm measurement step 1.

In the above example, various warnings and data validation were described. Typically, the warnings and data validation are based upon the manufacturer's recommendations for a stent graft, or perhaps a family of stent grafts. However, additional warnings can be added based upon clinical knowledge, or other knowledge known about stent-graft placement. Accordingly, the warnings and data validation described above are illustrative only and are not intended to limit the invention to the specific examples presented. In each instance, this information is stored in stent-graft database 114 and retrieved and displayed at the appropriate point in aneurysm measurement step 1.

Similarly, the various diameters and lengths that are entered in aneurysm measurement step 1 may be different for different stent grafts. For each stent graft, diameters and lengths that are entered in aneurysm measurement step 1 are those necessary to select a properly sized stent graft for a particular manufacturer. According, the examples in aneurysm measurement step 1 are illustrative only and are not intended to limit aneurysm measurement step 1 to the specific diameters and lengths described above. In view of this disclosure and the manufacturer's description of a particular stent graft, those of skill in the art can configure the graphic user interfaces used in aneurysm measurement step 1 for input of the data necessary as specified in that manufacturer's stent-graft specifications.

Figure 14:
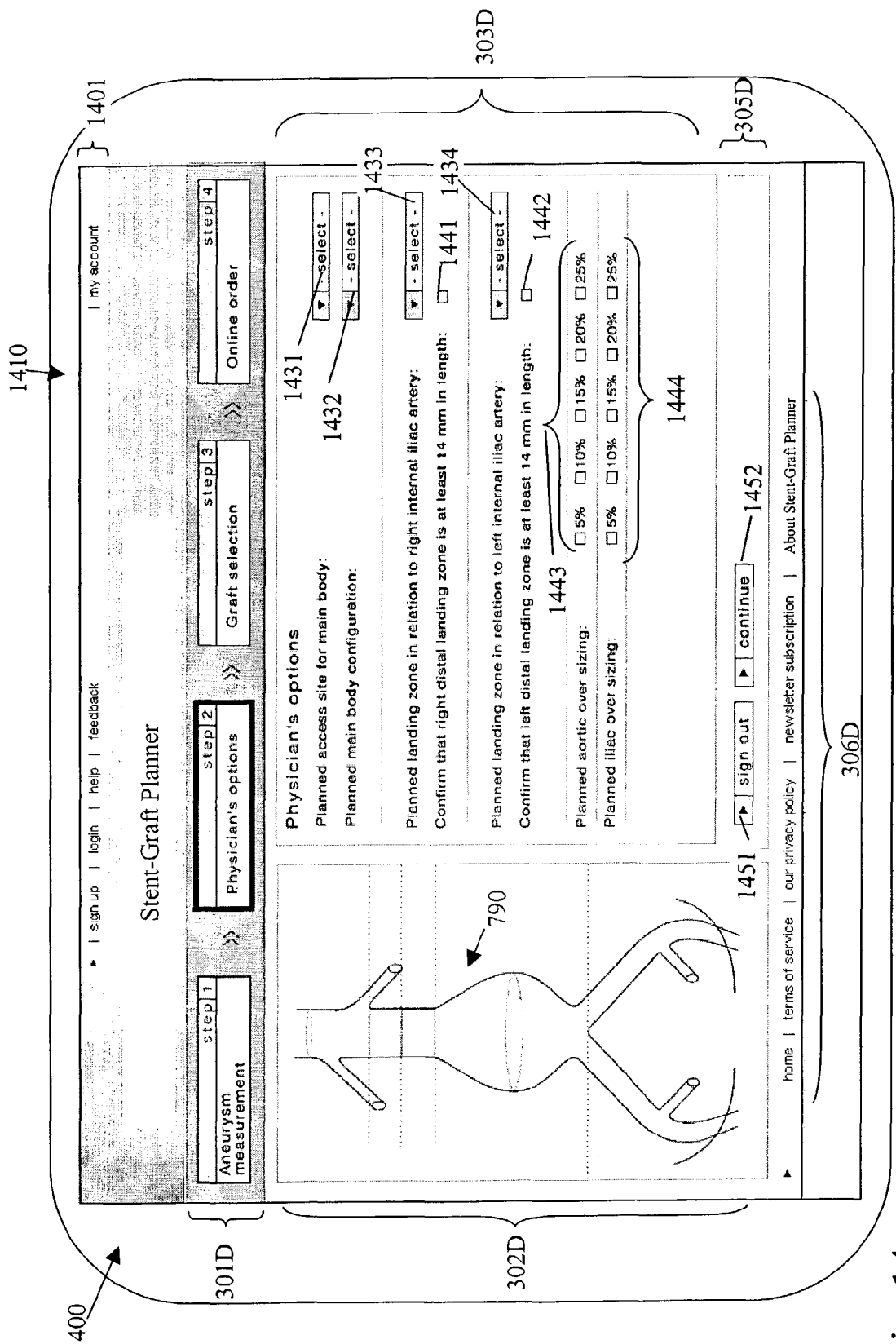
FIG. 14 is an example of a physician's options graphic user interface displayed on a display device.

Upon completion of aneurysm measurement step 1, physician's options graphic user interface 1410 (FIG. 14) is displayed. Physician's options graphic user interface 1410 includes the regions as described above for FIG. 3, i.e., regions 301D, 302D, 303D, 305D, 306D. In this example, other information options region 306D is the same as region 306A (FIG. 7) and that description is incorporated by reference herein. Another information options region 1401 includes links to sign up, login, help, feedback, and my account.

In stent-graft planning progress guide region 301D, four steps are again illustrated, aneurysm measurement step 1, physician's options step 2, graft selection step 3, and online order step. 4. Physician's options step 2 is highlighted.

Real-time graphic region 302D includes aortic aneurysm graphic 790 using the dimensions and shading generated in response to the data collected in aneurysm measurement step 1.

Data entry region 303D does include four pull down menus 1431, 1432, 1433, 1434, two check boxes 1441, 1442, a first plurality of check boxes 1443, and a second plurality of check boxes 1444.

A planned access site for main body Paccess is selected using pull down menu 1431. The options in pull down menu 1431 are: right; and left. The user selects one of the options in pull down menu 1431.

A planned main body configuration Pconfig is selected using pull down menu 1432. The options in pull down menu 1432 are: straight; and >90° twist, in this example. The user selects one of the options in pull down menu 1432. If the user selects >90° twist, a comment is presented in physician's options graphic user interface concerning the shortening of the graft, e.g., ">90° twist shortens graft about 10 mm."

A planned landing zone in relation to right internal iliac artery PiliaclandR is selected using pull down menu 1433. The options in pull down menu 1433 are proximal; distal; and _____ mm. The user selects one of proximal and distal and enters a distance in millimeters. If distal is selected, the distance entered is given a negative value in subsequent processing. The distance entered is checked to determine whether the value is in a range of permitted values, e.g., greater than zero mm and less than 70 mm. If the distance entered is not in this range, the value is flagged and the user is asked to recheck the input value.

The user checks checkbox 1441 to confirm that the right distal landing zone is at least 14 mm in length. If the user fails to check checkbox 1441, a warning is provided, e.g., "Confirm that chosen landing zone is at least 14 mm long, if not please choose another landing site."

A planned landing zone in relation to left internal iliac artery PiliaclandL is selected using pull down menu 1434. The options in pull down menu 1434 are proximal; distal; and _____ mm. The user selects one of proximal and distal and enters a distance in millimeters. If distal is selected the distance entered is given a negative value in subsequent processing. The distance entered is checked to determine whether the value is in a range of permitted values, e.g., greater than zero mm and less than 70 mm. If the distance entered is not in this range, the value is flagged and the user is asked to recheck the input value.

The user checks checkbox 1442 to confirm that the left distal landing zone is at least 14 mm in length. If the user fails to check checkbox 1441, a warning is provided, e.g., "Confirm that chosen landing zone is at least 14 mm long, if not please choose another landing site."

Plurality of checkboxes 1443 provide a range of planned aortic over sizing values, e.g., 5%, 10%, 15%, 20%, an 25% for planned aortic over sizing Paortasizing. If the user has a preference registered with the stent-graft planner site, the box corresponding to the preference is selected as the default. When the user confirms or makes a selection, a comment is provided in physician's options graphic user interface 1410, e.g., "Manufacturer recommends 10 to 15% over sizing based on measurements from CT or MR images." The selected value of planned aortic over sizing Paortasizing is stored as one plus the decimal value of the percentage, e.g., for 25%, 1.25 is saved.

Plurality of checkboxes 1444 provide a range of planned iliac over sizing values, e.g., 5%, 10%, 15%, 20%, an 25% for planned iliac over sizing Piliacsizing. If the user has a preference registered with the stent-graft planner site, the box corresponding to the preference is selected as the default. When the user confirms or makes a selection, a comment is provided in physician's options graphic user interface 1410, e.g., "Manufacturer recommends 10 to 15% over sizing based on measurements from CT or MR images." The selected value of planned aortic over sizing Piliacsizing is stored as one plus the decimal value of the percentage, e.g., for 25%, 1.25 is saved.

After valid data has been entered for all of the items in physician's options graphic user interface 1410, continue button 1452, in this example, is activated in navigation region 305D. In this example, navigation region 305D includes a sign out button 1451 and continue button 1452. Sign out button 1451 is always active. Alternatively, continue button 1452 may also be always active.

If the user selects sign out button 1451, a pop-up window appears and asks the user to confirm the sign out request or whether the user wants to select a new stent graft. If the user confirms the sign out request, all the data that has been entered and a reference to the current graphic user interface are saved in physician database 111 so that the session can be restarted later.

Figure 15:
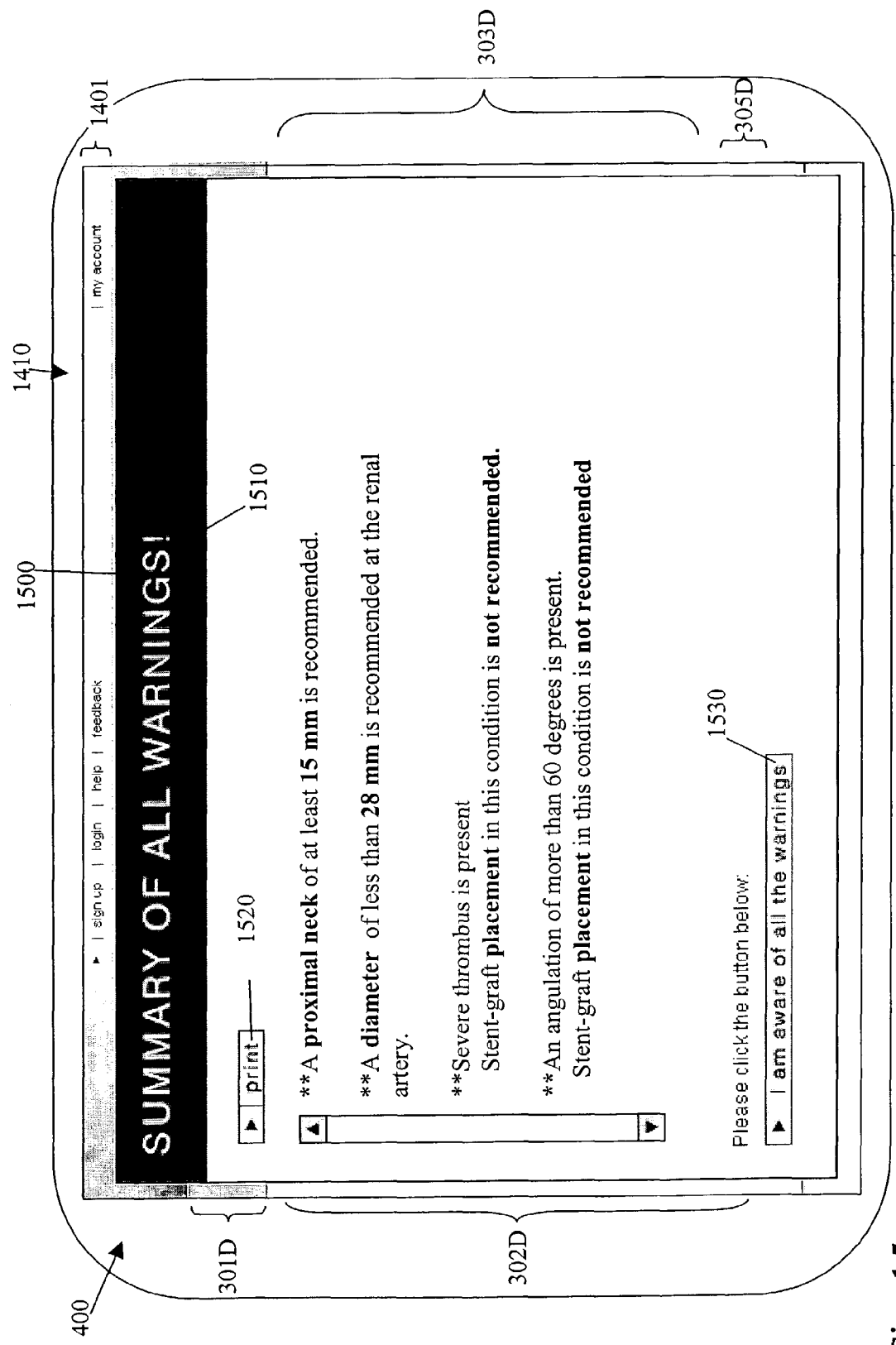
FIG. 15 is an example of a summary warning pop-up window.

If the user selects continue button 1452, the data entered on physician's options graphic user interface 1410 is saved in database 111 along with any warnings that were generated. All of the data to characterize the aortic aneurysm has been entered, and in this example, before selecting a stent, a summary of the warning are presented in pop-up window 1500 (FIG. 15). Pop-up window 1500 includes a warning bar that has a bright red color. Pop-up window 1500 includes each of the warnings that have been generated. The user can print the warning summary by selecting print button 1520. To continue with the stent-graft selection, the user must select the "I am aware of the warnings" button 1530.

At this point all the information to select a stent graft is available, the user has accepted the warnings, and so device selection option operation 203 is started in the background. A ZENITH stent graft manufactured by Cook Incorporated, Bloomington, Ind. (ZENITH is a trademark of Cook Incorporated.) is used as an example. This stent graft is a bifurcated aortoiliac stent graft. The device is a supported, bifurcated, self-expandable stent graft with multiple stainless steel Z stents placed inside the graft with a proximal bare stent that can be placed across the renal arteries. The device has an array of extension sizes and diameters.

The ZENITH stent graft ranges from 22 to 32 mm in diameter using an introducer of 18 to 20 French sizes. The extensions range from 8 to 24 mm and are deployed through a 14 to 16 French sheath.

For this example, a specification is available for determining the ideal graft. The specification defines a proximal graft diameter GDprox that is equal to aorta diameter at the lowest renal artery D0 multiplied by planned aorta over sizing Paortasizing, i.e., $$GDprox = D0 * Paortasizing.$$

A length of right limb GLlimbR is defined that is equal to lowest renal artery to right internal iliac artery Lto_intR minus planned landing zone in relation to right internal iliac artery PiliaclandR(mm), i.e., GLlimbR=Lto_intR−PiliaclandR(mm).

However, if the value of planned main body configuration Pconfig is >90° twist, 10 mm is subtracted, i.e., GLlimbR=Lto_intR−PiliaclandR(mm)−10 mm when planned main body configuration Pconfig is >90° twist.

A length of left limb GLlimbL is defined that is equal to lowest renal artery to left internal iliac artery Lto_intL minus planned landing zone in relation to left internal iliac artery PiliaclandL(mm), i.e., GLlimbL=Lto_intL−PiliaclandL(mm).

However, if the value of planned main body configuration Pconfig is >90° twist, 10 mm is subtracted, i.e., GLlimbL=Lto_intL−PiliaclandL(mm)−10 mm when planned main body configuration Pconfig is >90° twist.

Right distal graft diameter GDdistR is defined as right common iliac artery diameter DcomR multiplied by planned iliac over sizing Piliacsizing if planned landing zone in relation to right internal iliac artery PiliaclandR is proximal, and is defined as right external iliac artery diameter DextR multiplied by planned iliac over sizing Piliacsizing if planned landing zone in relation to right internal iliac artery PiliaclandR is distal. Specifically, GDdistR=DcomR*Piliacsizing if PiliaclandR is proximal, or GDdistR=DextR*Piliacsizing if PiliaclandR is distal.

Similarly, left distal graft diameter GDdistL is defined as left common iliac artery diameter DcomL multiplied by planned iliac over sizing Piliacsizing if planned landing zone in relation to left internal iliac artery PiliaclandL is proximal, and is defined as left external iliac artery diameter DextL multiplied by planned iliac over sizing Piliacsizing if planned landing zone in relation to left internal iliac artery PiliaclandL is distal. Specifically, GDdistL=DcomL*Piliacsizing if PiliaclandL is proximal, or GDdistL=DextL*Piliacsizing if PiliaclandL is distal.

With these values, the ZENITH stent graft suggested main body TFB-"x1"-"y1" is selected for sizing, where x1 is the main body graft diameter and y1 is the main body graft length. Main body graft diameter x1 is determined by using lowest renal artery to the aortic bifurcation length Lto_bif to select a value of main body graft diameter x1 from TABLE 5.

TABLE 5

| Value of Lto_bif | Value of x1 selected |
|---|---|
| >80 mm and ≦95 mm | 1 |
| >95 mm and ≦110 mm | 2 |
| >110 mm and ≦125 mm | 3 |
| >125 mm and ≦140 mm | 4 |
| >140 mm and ≦155 mm | 5 |

The value of proximal graft diameter GDprox is rounded up to the next even number, i.e., to one of the following numbers: 22, 24, 26, 28, 30, 32. The rounded value of proximal graft diameter GDprox is to select main body graft length y1 from TABLE 6.

TABLE 6

| Value of rounded GDprox | Value of y1 selected |
|---|---|
| 22 mm | 22 |
| 24 mm | 23 |
| 26 mm | 26 |
| 28 mm | 28 |
| 30 mm | 30 |
| 32 mm | 32 |

Next, the ZENITH stent graft suggested contralateral leg TFLE-"x2"-"y2" is selected for sizing where x2 is contralateral leg graft diameter and y2 is the contralateral leg graft working length. The dimensions used in selecting contralateral leg TFLE-"x2"-"y2" depends on the value of planned access site for main body Paccess. the contralateral lag is the leg that is the opposite of the value of planned access site for main body Paccess.

If planned access site for main body Paccess is night, graft diameter distal contralateral side GDdistcontralat is left distal graft diameter GDdistL. Graft length contralateral side GLlimbcontralat is length of left limb GLlimbL.

Conversely, if planned access site for main body Paccess is left, graft diameter distal contralateral side GDdistcontralat is right distal graft diameter GDdistR. Graft length contralateral side GLlimbcontralat is length of right limb GLlimbR.

After graft diameter distal contralateral side GDdistcontralat is determined, graft diameter distal contralateral side GDdistcontralat is rounded up to the next even number, i.e., rounded up to the next of following numbers: 8, 10, 12, 14, 16, 18, 20, 22, and 24. The rounded value of graft diameter distal contralateral side GDdistcontralat is used to select contralateral leg graft diameter x2 from TABLE 7.

TABLE 7

| Value of rounded GDdistcontralatt | Value of x2 selected |
|---|---|
| 8 mm | 8 |
| 10 mm | 10 |
| 12 mm | 12 |
| 14 mm | 14 |
| 16 mm | 16 |
| 18 mm | 18 |
| 20 mm | 20 |
| 22 mm | 22 |
| 24 mm | 24 |

Next, a correlation fact c1 is selected from TABLE 8 using the value of main body graft diameter x1 selected from TABLE 5.

TABLE 8

| Value of x1 selected from TABLE 1 | Value of c1 |
|---|---|
| 1 | 74 mm |
| 2 | 88 mm |
| 3 | 103 mm |
| 4 | 117 mm |
| 5 | 132 mm |

A contralateral working length WLcontralat is defined as graft length contralateral side GLlimbcontralat minus correction factor c1. After contralateral working length WLcontralat is determined, contralateral working length WLcontralat is rounded down to the next of the following numbers: 37, 54, 71, 88, 105, and 122. The rounded value of contralateral working length WLcontralat is used to select contralateral leg working length y2 from TABLE 9.

TABLE 9

| Value of rounded WLcontralat | Value of y2 selected |
|---|---|
| 37 mm | 37 |
| 54 mm | 54 |
| 71 mm | 71 |
| 88 mm | 88 |
| 105 mm | 105 |
| 122 mm | 122 |

If the value of contralateral leg graft diameter x2 selected from TABLE 7 is greater than 12, the maximum contralateral leg working length y2 is 88 mm. In this case y2 is set to 88 and if contralateral leg working length y2 selected from TABLE 9 was greater than 88, the working length is too short.

If the working length is too short, an additional extender TFLE 12-"z1" is added, where z1 is the contralateral working length. An additional missing working length addMissWL is defined as unrounded contralateral working length WLcontralat minus the value of y2. (The extender length is missing working length plus 40 mm (20 mm overlap on both sides).)

After additional missing working length addMissWL is determined, additional missing working length addMissWL is rounded up to the next of the following numbers: 14, 31, 48, 65, 82. The rounded value of additional missing working length addMissWL is used to select contralateral extender working length z1 from TABLE 10.

TABLE 10

| Value of rounded addMissWL | Value of z1 selected |
|---|---|
| 14 mm | 54 |
| 31 mm | 71 |
| 48 mm | 88 |
| 65 mm | 105 |
| 82 mm | 122 |

Next, the ZENITH stent graft suggested ipsilateral leg TFLE-"x3"-"y3" is selected for sizing, where x3 is the ipsilateral leg graft diameter, and y3 is the ipsilateral leg working length. The dimensions used in selecting ipsilateral leg TFLE-"x3"-"y3" depends on the value of planned access site for main body Paccess. The ipsilateral side is the value of planned access site for main body Paccess.

If planned access site for main body Paccess is right, graft diameter distal ipsilateral side GDdistipsilat is right distal graft diameter GDdistR. Graft length ipsilateral side GLlimbipsilat is length of right limb GLlimbR.

Conversely, if planned access site for main body Paccess is left, graft diameter distal ipsilateral side GDdistipsilat is left distal graft diameter GDdistL. Graft length ipsilateral side GLlimbipsilat is length of left limb GLlimbL.

After graft diameter distal ipsilateral side GDdistipsilat is determined, graft diameter distal ipsilateral side GDdistipsilat is rounded up to the next even number, i.e., rounded up to the next of following numbers: 8, 10, 12, 14, 16, 18, 20, 22, and 24. The rounded value of graft diameter distal ipsilateral side GDdistipsilat is used to select ipsilateral leg graft diameter x3 from TABLE 11.

TABLE 11

| Value of rounded GDdistipsilat | Value of x3 selected |
|---|---|
| 8 mm | 8 |
| 10 mm | 10 |
| 12 mm | 12 |
| 14 mm | 14 |
| 16 mm | 16 |
| 18 mm | 18 |
| 20 mm | 20 |
| 22 mm | 22 |
| 24 mm | 24 |

Next, a correction fact i1 is selected from TABLE 12 using the value of main body graft diameter x1 selected from TABLE 5.

TABLE 12

| Value of x1 selected from TABLE 1 | Value of i1 |
|---|---|
| 1 | 104 mm |
| 2 | 118 mm |
| 3 | 133 mm |
| 4 | 147 mm |
| 5 | 162 mm |

An ipsilateral working length WLipsilat is defined as graft length ipsilateral side GLlimbipsilat minus correction factor i1. After ipsilateral working length WLipsilat is determined, ipsilateral working length WLipsilat is rounded down to the next of the following numbers: 37, 54, 71, 88, 105, and 122. The rounded value of ipsilateral working length WLipsilat is used to select ipsilateral leg working length y3 from TABLE 13.

TABLE 13

| Value of rounded WLipsilat | Value of y3 selected |
|---|---|
| 37 mm | 37 |
| 54 mm | 54 |
| 71 mm | 71 |
| 88 mm | 88 |
| 105 mm | 105 |
| 122 mm | 122 |

If the value of ipsilateral leg graft diameter x3 selected from TABLE 11 is greater than 12, the maximum ipsilateral leg working length y3 is 88 mm and so ipsilateral leg working length y3 is set to 88. If the value of ipsilateral length y3 selected from TABLE 13 was greater than 88 mm, the working length is too short.

If the working length is too short, an additional extender TFLE 12-"z2" is added, where z2 is the ipsilateral extender working length. An additional missing working length addMissWL is defined as unrounded ipsilateral working length WLipsilat minus the value of ipsilateral leg working length y3. (The extender length is missing working length plus 40 mm (20 mm overlap on both sides).)

After additional missing working length addMissWL is determined, additional missing working length addMissWL is rounded up to the next of the following numbers: 14, 31, 48, 65, 82. The rounded value of additional missing working length addMissWL is used to select ipsilateral extender working length z2 from TABLE 14.

TABLE 14

| Value of rounded addMissWL | Value of z2 selected |
|---|---|
| 14 mm | 54 |
| 31 mm | 71 |
| 48 mm | 88 |
| 65 mm | 105 |
| 82 mm | 122 |

The above example is illustrative and is not intended to limit the invention to this specific stent graft. In view of this disclosure, one of skilled in the art can use manufacturer's information for other stent grafts and implement a method to select a stent graft using the collected measurements and information.

This completes the selection of the stent graft, and graft selection graphic user interface 1610 (FIG. 16) is presented on display 400 with an image of the suggested stent graft displayed in real-time graphics region 302E in the image of the vessels. FIG. 17A is an example of a graphic of a narrowed (stenotic) aorta 1700. FIG. 17B illustrates an example of a graphic image of stent graft 1750 placed in graphic of narrowed (stenotic) aorta 1700. Accordingly, the examples in FIG. 16 and the subsequent figures are illustrative only and are not intended to limit the invention to the specific vessels and stent graft displayed.

Figure 16:
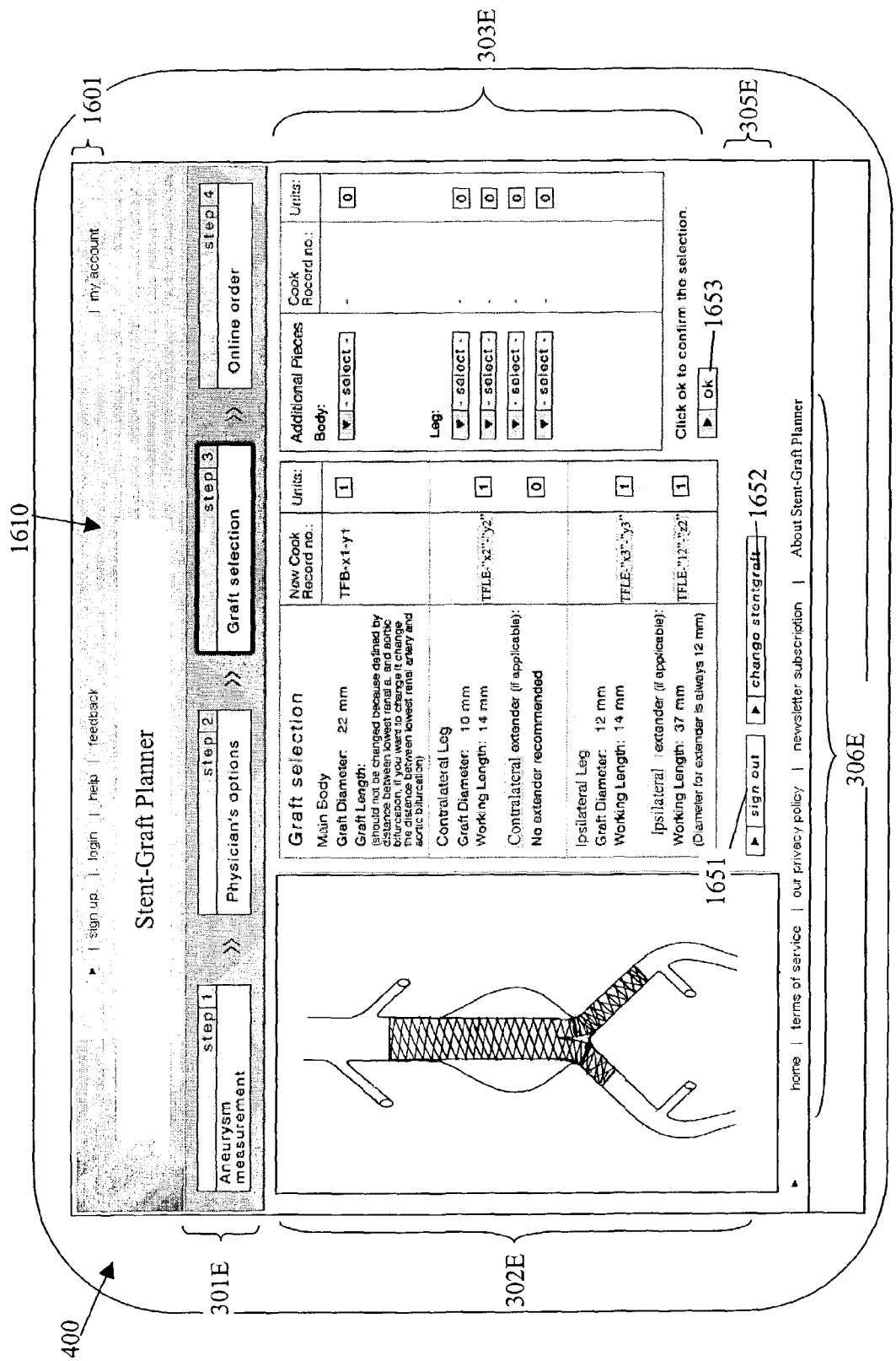
FIG. 16 is an example of a graft selection graphic user interface displayed on a display device.
Figure 17A:
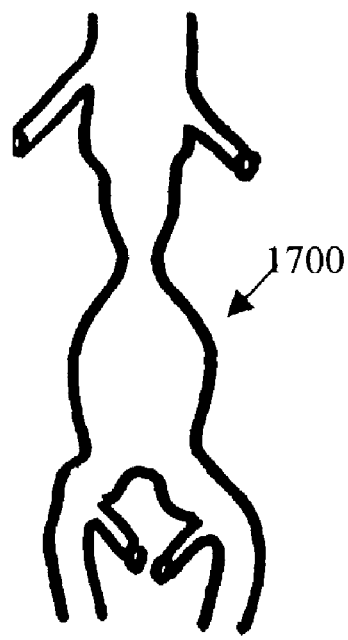
FIG. 17A is an example of a graphic of a narrowed (stenotic) aorta.
Figure 17B:
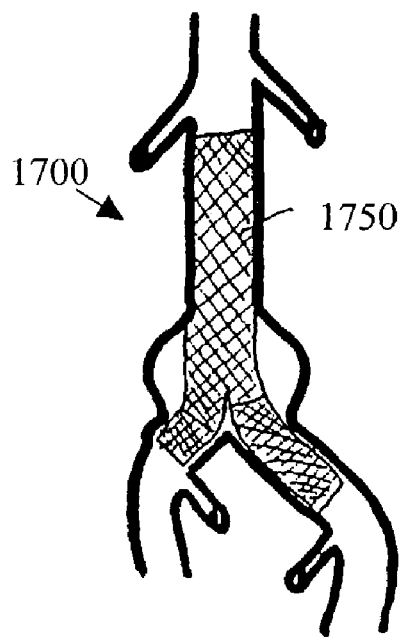
FIG. 17B illustrates an example of a stent graft placed in the narrowed (stenotic) aorta of FIG. 17A.

In FIG. 16, the length of the displayed contralateral leg Contralatleg is:

Contralatleg=$c1$+"$y2$"

or

Contralatleg=$c1$+"$y2$"+"$z1$"

if the extender was suggested. The length of the displayed ipsilateral leg Ipsilatleg is:

Ipsilatleg=$i1$+"$y3$"

or

Ipsilatleg=$i1$+"$y3$"+"$z2$"

if the extender was suggested. The stent-graft diameter is adjusted to the vessels' diameter, because the stent graft, in this example, is self-expanding. Care is taken to represent the lengths accurately so that the physician has a good visual representation of the stent-graft location relative to the various arteries. Thus, an accurate evaluation of the suitability of the suggest stent graft can be made.

Graft selection graphic user interface 1610 (FIG. 16) includes the regions as described above for FIG. 3, i.e., regions 301E, 302E, 303E, 305E, 306E. In this example, other information options region 306E is the same as region 306A (FIG. 7) and that description is incorporated by reference herein. Another information options region 1601 includes links to sign up, login, help, feedback, and my account.

In stent-graft planning progress guide region 301E, four steps are again illustrated, aneurysm measurement step 1, physician's options step 2, graft selection step 3, and online order step 4. Graft selection step 3 is highlighted.

Data input region 303E includes an indication of each of the graft parts selected and a suggested number of units for each part selected. The dimensions for each of the parts are also presented.

In this example, main body, TFB-"$x1$"-"$y1$" is suggested with diameter of 22 mm. Contralateral iliac leg TFLE-"$x2$"-"$y2$" is suggested with a graft diameter of 10 mm and a working length of 14 mm. An ipsilateral iliac leg TFLE-"$x3$"-"$y3$" is suggested with a graft diameter of 12 mm and a working length of 14 mm. No contralateral extender is suggested. An ipsilateral extender TFLE-12-"$z2$" is suggested with a working length of 37 mm. The user is also notified that the length of the main body should not be changed.

Figure 18:
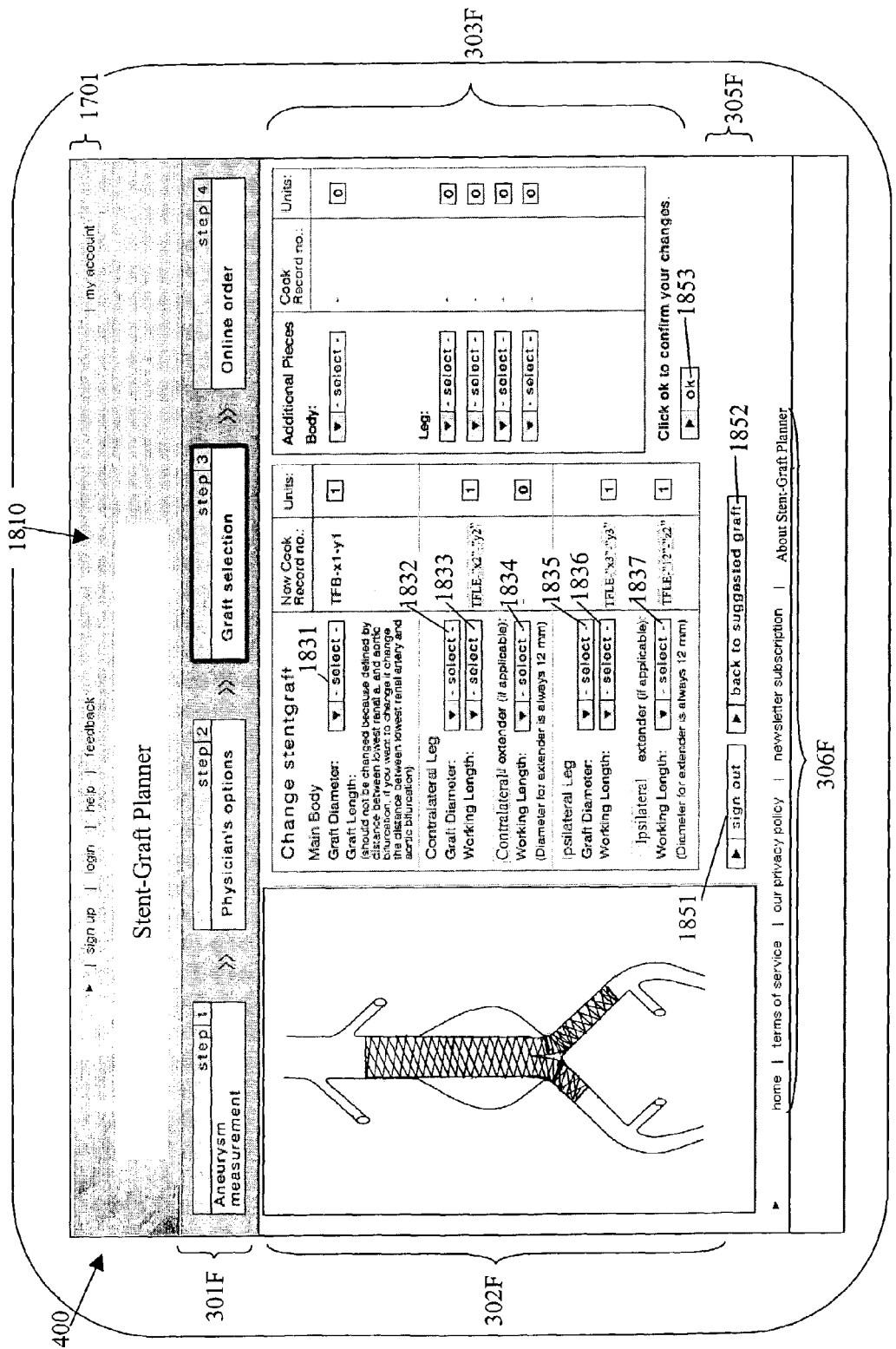
FIG. 18 is an example of a change stent graft graphic user interface displayed on a display device.

Navigation region 305E of graft selection graphic user interface 1610 includes an ok button 1653, a sign out button 1651, and change stentgraft button 1652. If the user selects ok button, the user goes to order online step 4, as described more completely below. Sign out button 1651 functions as described above for the other sign out buttons. If the user selects change stent graft button 1652, the user is presented change stent graft graphic user interface 1810 (FIG. 18).

Change stent graft graphic user interface 1810 includes the regions as described above for FIG. 3, i.e., regions 301F, 302F, 303F, 305F, 306F. In this example, other information options region 306F is the same as region 306A (FIG. 7) and that description is incorporated by reference herein. Another information options region 1801 includes links to sign up, login, help, feedback, and my account.

In stent-graft planning progress guide region 301F, four steps are again illustrated, aneurysm measurement step 1, physician's options step 2, graft selection step 3, and online order step 4. Graft selection step 3 is still highlighted.

Real-time graphic region 302F includes the 2-D image of the aortic aneurysm with the suggested stent graft in place.

Data input region 303F includes an indication of each of the suggested graft parts selected and a suggested number of units for each suggested part. In this example, main body, TFB-"$x1$"-"$y1$" is suggested and has a graft diameter pull-down menu 1831. Contralateral iliac leg TFLE-"$x2$"-"$y2$" is suggested and has a graft diameter pull down menu 1832 and a working length pull down menu 1833.

An ipsilateral iliac leg TFLE-"$x3$"-"$y3$" is suggested with a graft diameter pull down menu 1835 and a working length pull down menu 1836. No contralateral extender is suggested, but there is a contralateral extender working length pull down menu 1834. An ipsilateral extender TFLE-12-"$z2$" is suggested with a working length pull down menu 1837. The user is also notified that the length of the main body should not be changed.

For this stent graft, main body graft diameter pull-down menu 1831 includes 22, 24, 26, 28, 30, 32 mm diameters. The user can select one value. The current value of main body graft diameter $x1$ is the default selection. If the user selects a different value, main body graft diameter $x1$ is set to that value.

For this stent graft, contralateral leg graft diameter pull-down menu 1832 includes 8, 10, 12, 14, 16, 18, 20, 22, 24 mm diameters. The user can select one value. The current value of contralateral leg graft diameter $x2$ is the default selection. If the user selects a different value, contralateral leg graft diameter $x2$ is set to that value.

For this stent graft, contralateral leg working length pull-down menu 1833 allows changes to the length in 17 mm steps. Thus, the options include no change, add 17 mm, and shorten 17 mm. The default selection is no change. The current value of contralateral leg working length $y2$ and the option selected from pull-down menu 1833 are used to select a new value of contralateral leg working length $y2$ from with TABLE 15.

TABLE 15

| Current value of $y2$ | Option Selected from menu 1833 | New Value of $y2$ |
|---|---|---|
| $y2$ | No change | $y2$ |
| 37 mm | add 17 | 54 |
| 37 mm | shorten 17 | 37* |
| 54 mm | add 17 | 71 |
| 54 mm | shorten 17 | 37 |
| 71 mm | add 17 | 88 |
| 71 mm | shorten 17 | 54 |
| 88 mm | add 17 | 105 |
| 88 mm | shorten 17 | 71 |
| 105 mm | add 17 | 122 |
| 105 mm | shorten 17 | 88 |
| 122 mm | add 17 | 122** |
| 122 mm | shorten 17 | 105 |

*A comment is generated on change stent-graft graphic user interface 1810 indicating that this change is not permitted because the value of contralateral leg working length $y2$ is already the shortest available.
**A comment is generated on change stent-graft graphic user interface 1810 indicating that this change is not permitted because the value of contralateral leg working length $y2$ is already the longest available.

As explained above, if the current value of contralateral leg diameter $x2$ is greater than 12, the maximum contralateral leg working length $y2$ is 88 mm. In this case, contralateral leg working length $y2$ is set to 88 and if contralateral leg working length $y2$ selected from TABLB 15 was greater than 88, the working length is too short. Accordingly, an evaluation, as described above, is done to determine whether an extender is necessary.

For this stent graft, ipsilateral leg graft diameter pull-down menu 1835 includes 8, 10, 12, 14, 16, 18, 20, 22, 24 mm diameters. The user can select one value. The current value of ipsilateral leg graft diameter $x3$ is the default selection. If the user selects a different value, ipsilateral leg graft diameter $x3$ is set to that value.

For this stent graft, ipsilateral leg working length pull-down menu 1836 allows changes to the length in 17 mm steps. Thus, the options include no change, add 17 mm, and shorten 17 mm. The default selection is no change. The current value of ipsilateral leg working length $y3$ and the option selected from pull-down menu 1833 are used to select a new value of ipsilateral leg working length $y3$ from with TABLE 16.

TABLE 16

| Current value of $y3$ | Option Selected from menu 1836 | New Value of $y3$ |
|---|---|---|
| $y3$ | no change | $y3$ |
| 37 mm | add 17 | 54 |
| 37 mm | shorten 17 | 37* |
| 54 mm | add 17 | 71 |
| 54 mm | shorten 17 | 37 |
| 71 mm | add 17 | 88 |
| 71 mm | shorten 17 | 54 |
| 88 mm | add 17 | 105 |
| 88 mm | shorten 17 | 71 |
| 105 mm | add 17 | 122 |
| 105 mm | shorten 17 | 88 |
| 122 mm | add 17 | 122** |
| 122 mm | shorten 17 | 105 |

*A comment is generated on change stent-graft graphic user interface 1810 indicating that this change is not permitted because the value of ipsilateral leg working length $y3$ is already the shortest available.
**A comment is generated on change stent-graft graphic user interface 1810 indicating that this change is not permitted because the value of ipsilateral leg working length $y3$ is already the longest available.

As explained above, if the current value of ipsilateral leg diameter $x3$ greater than 12, the maximum ipsilateral leg working length $y3$ is 88 mm. In this case, ipsilateral leg working length $y3$ is set to 88 and if ipsilateral leg working length $y3$ selected from TABLE 16 was greater than 88, the working length is too short. Accordingly, an evaluation, as described above, is done to determine whether an extender is necessary for the working length of the ipsilateral leg.

For this stent graft, contralateral extender length pull-down menu 1834 allows changes to the length in 17 mm steps. Thus, the options include no change, add 17 mm, and shorten 17 mm. The default selection is no change. The current value of contralateral extender working length $z1$ and the option selected from pull-down menu 1834 are used to select a new value of contralateral extender working length $z1$ from with TABLE 17.

TABLE 17

| Current value of $z1$ | Option Selected from menu 1834 | New Value of $z1$ |
|---|---|---|
| $z1$ | No change | $z1$ |
| 54 mm | add 17 | 71 |
| 54 mm | shorten 17 | 54* |
| 71 mm | add 17 | 88 |
| 71 mm | shorten 17 | 54 |
| 88 mm | add 17 | 105 |
| 88 mm | shorten 17 | 71 |
| 105 mm | add 17 | 122 |
| 105 mm | shorten 17 | 88 |
| 122 mm | add 17 | 122** |
| 122 mm | shorten 17 | 105 |

*A comment is generated on change stent-graft graphic user interface 1810 indicating that this change is not permitted because the value of contralateral extender working length $z1$ is already the shortest available.
**A comment is generated on change stent-graft graphic user interface 1810 indicating that this change is not permitted because the value of contralateral extender working length $z1$ is already the longest available.

For this stent graft, ipsilateral extender length pull-down menu 1837 allows changes to the length in 17 mm steps. Thus, the options include no change, add 17 mm, and shorten 17 mm. The default selection is no change. The current value of ipsilateral extender working length $z2$ and the option selected from pull-down menu 1837 are used to select a new value of ipsilateral extender working length $z2$ from with TABLE 18.

TABLE 18

| Current value of $z2$ | Option Selected from menu 1837 | New Value of $z2$ |
|---|---|---|
| $z2$ | No change | $z2$ |
| 54 mm | add 17 | 71 |
| 54 mm | shorten 17 | 54* |
| 71 mm | add 17 | 88 |
| 71 mm | shorten 17 | 54 |
| 88 mm | add 17 | 105 |
| 88 mm | shorten 17 | 71 |
| 105 mm | add 17 | 122 |
| 105 mm | shorten 17 | 88 |
| 122 mm | add 17 | 122** |
| 122 mm | shorten 17 | 105 |

*A comment is generated on change stent-graft graphic user interface 1810 indicating that this change is not permitted because the value of ipsilateral extender working length $z2$ is already the shortest available.
**A comment is generated on change stent-graft graphic user interface 1810 indicating that this change is not permitted because the value of ipsilateral extender working length $z2$ is already the longest available.

When a change is made to the dimensions of the selected stent graft, the 2-D image of the aortic aneurysm with the stent-graft is updated to reflect the changes. As described above, care is taken to accurately depict the length of the stent graft.

Navigation region 305F of change stent-graft graphic user interface 1810 includes an ok button 1853, a sign out button 1851, and back to suggested stent graft button 1852. If the user selects ok button 1853, the user goes to order online step 4, as described more completely below. Sign out button 1851 functions as described above for the other sign out buttons. If the user selects back to suggested stent graft button 1852, the user is presented graft selection graphic user interface 1610 (FIG. 16).

Figure 19:
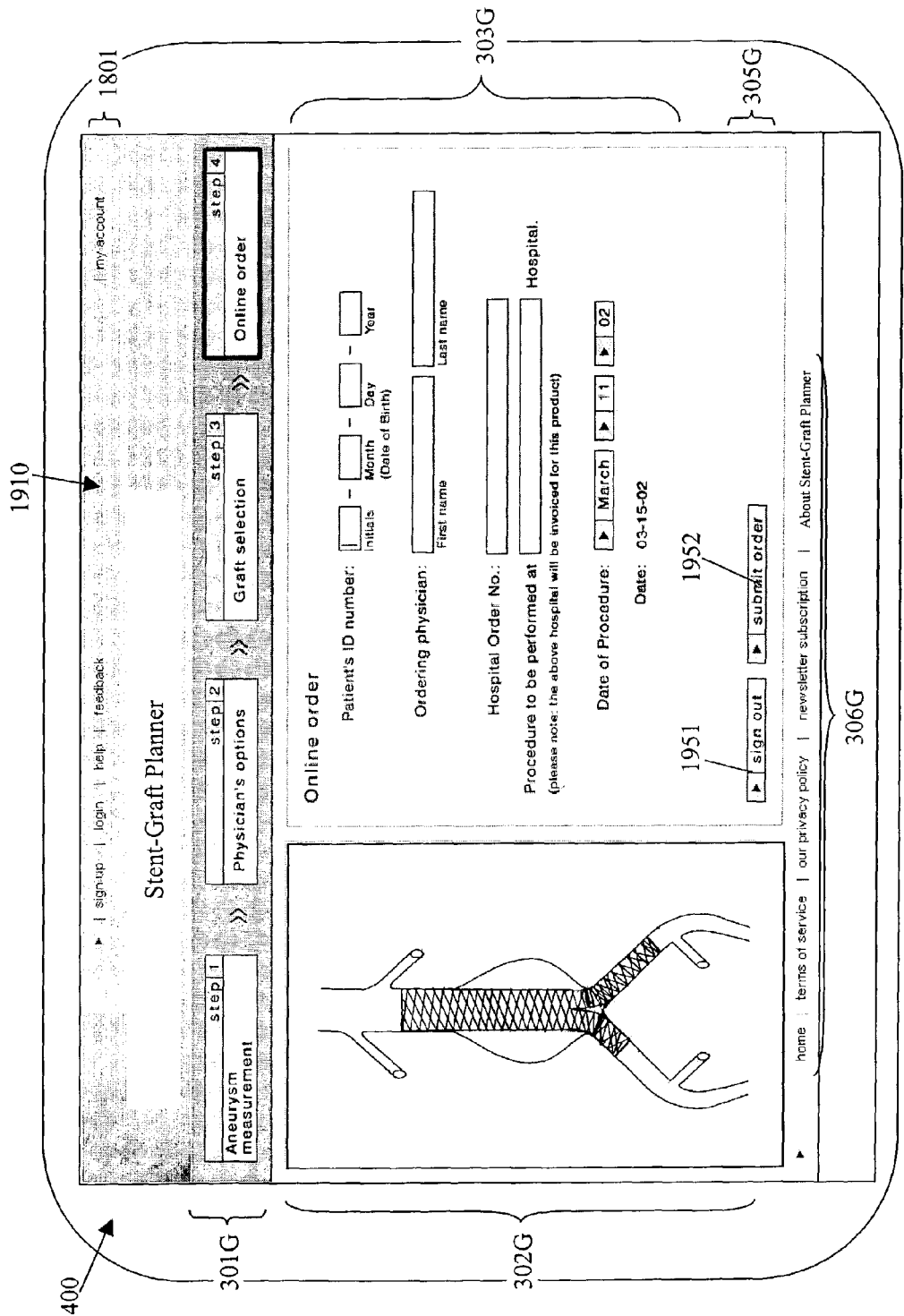
FIG. 19 is an example of an on line order graphic user interface displayed on a display device.

On line order graphic user interface 1910 (FIG. 19) includes the regions as described above for FIG. 3, i.e., regions 301G, 302G, 303G, 305G, 306G. In this example, other information options region 306G is the same as region 306A (FIG. 7) and that description is incorporated by reference herein. Another information options region 1901 includes links to sign up, login, help, feedback, and my account.

In stent-graft planning progress guide region 301G, four steps are again illustrated, aneurysm measurement step 1, physician's options step 2, graft selection step 3, and online order step 4. Order online step 4 is highlighted.

Data input region 303G includes fields for the user to associate the stent-graft selected with a particular patient and the user. Specifically, a patient's identifier field includes four windows: a patient's initials window; a patient's month of birth window; a patient's day of birth window; and a patient's year of birth window. The patient information in data input region 303G may be reduced or changed subject to interpretation of laws related to disclosure of patient information, i.e., HIPPA.

There is an ordering physician's first name window and an ordering physician's last name window. There also is a hospital order number window, and a procedure to be performed at hospital window. Finally, there are pull down menus for specifying the date of the procedure. The user completes each of these fields.

Figure 20:
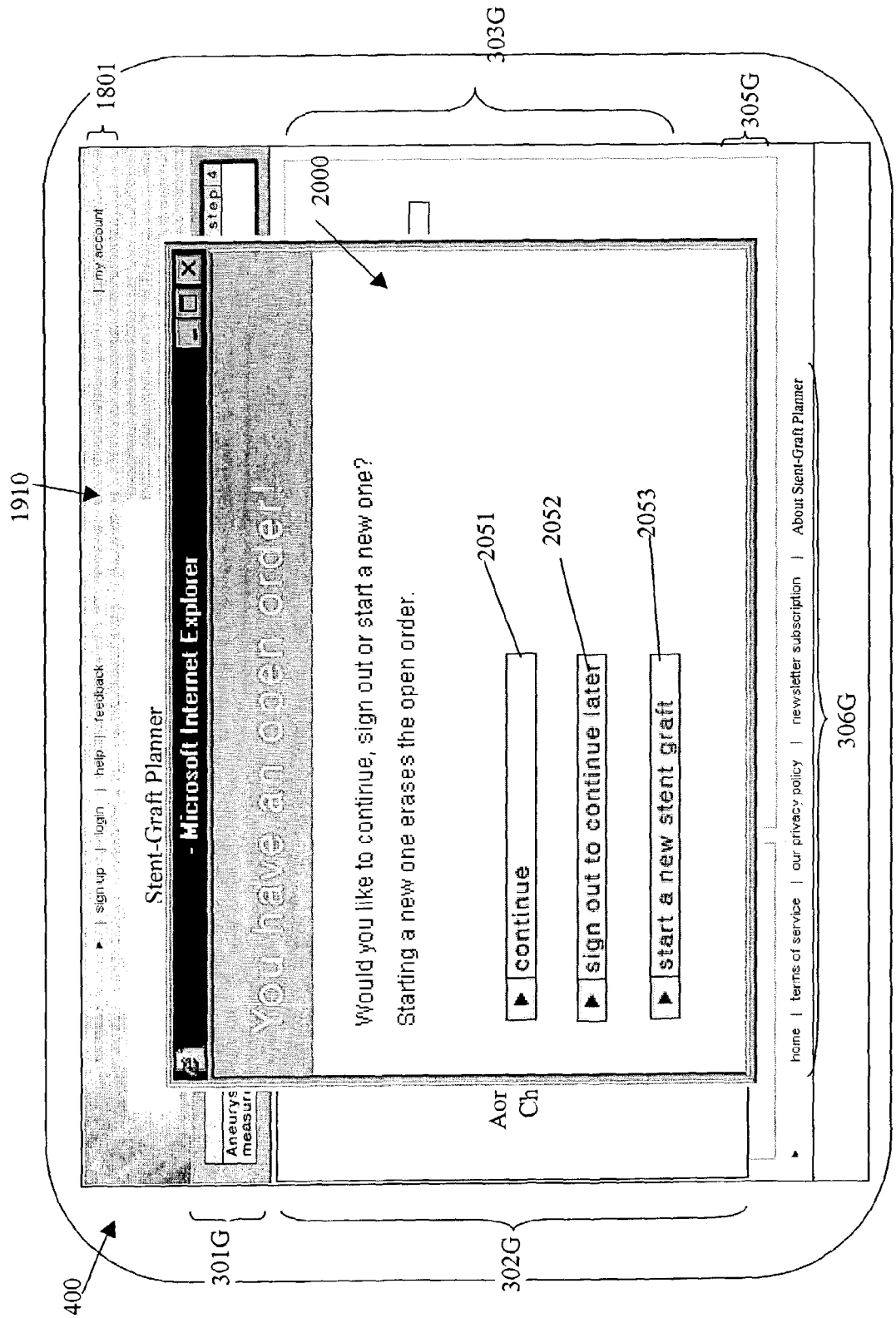
FIG. 20 is an example of an open order pop-up window.

Navigation region 305G of online order graphic user interface 1910 includes a sign out button 1951, and submit order button 1952. If the user selects sign out button 1951, open order pop-up window 2000 (FIG. 20) is displayed.

Open order pop-up window 2000 includes a continue button 2051, a sign out to continue later button 2052, and a start a new stent graft 2053. Selection of continue button 2051 continues with the online order, as described below. Selection of sign out to continue later button 2052 saves the present order and closes stent-graft planner site. Selection of start a new stent graft button 2053 saves the present order and initiates the graphic user interface to start process 200 over.

Returning to FIG. 19, if the user selects submit order 1952, an order is submitted to the manufacturer for the stent graft over Internet 104 (FIG. 1). This order is generated automatically. FIGS. 21A and 21B are an example of an automatically generated order form for the ZENITH stent graft. If a connection to the Internet is not available, the user is given the option of faxing the order from the user's computer, or alternatively printing out the order form for faxing by the user.

Figure 22:
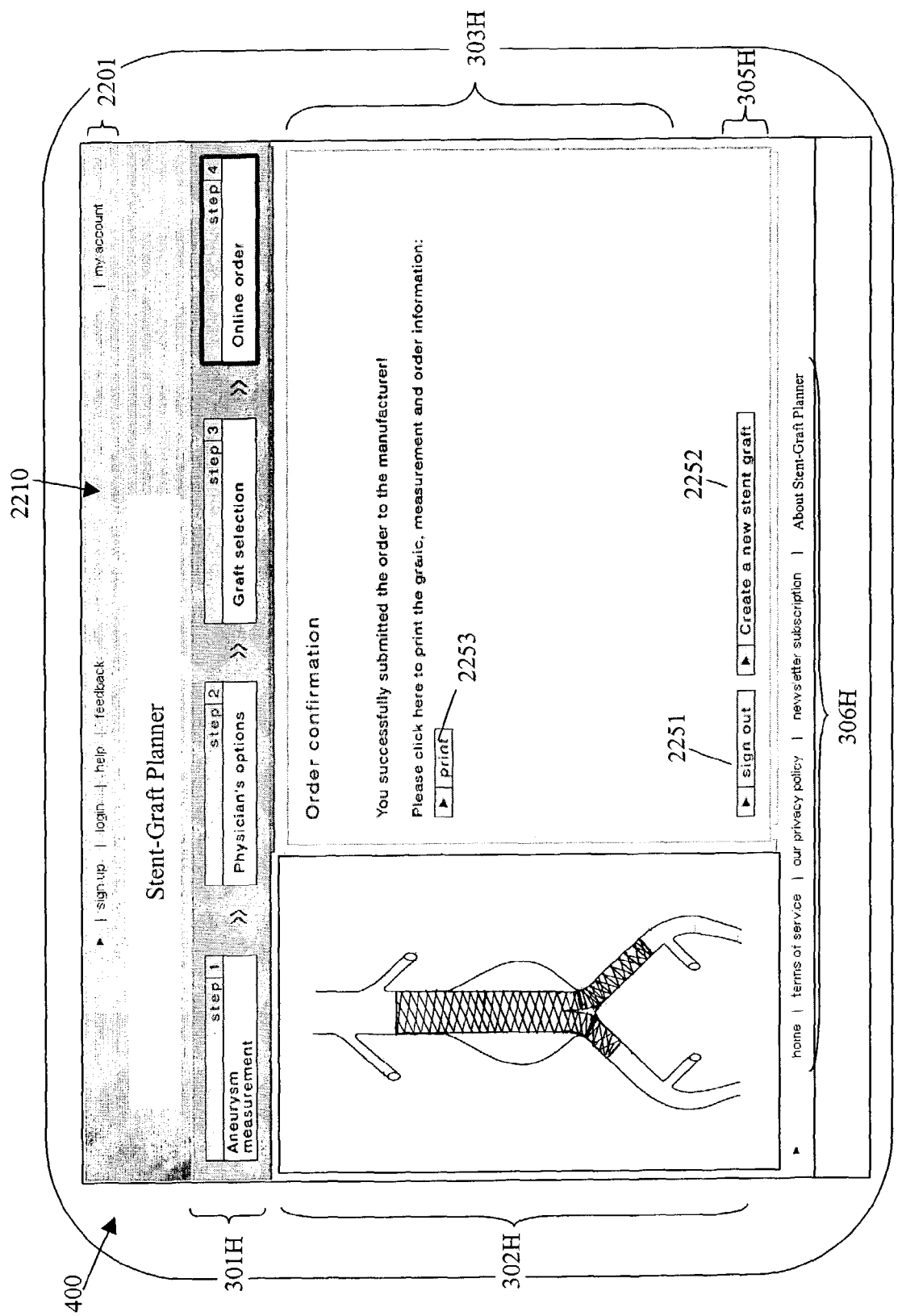
FIG. 22 is an example of an order confirmation graphic user interface displayed on a display device.

Assuming the order is transmitted vie Internet 104, the user is presented order confirmation graphic user interface 2210 (FIG. 22). Order confirmation graphic user interface 1910 includes the regions as described above for FIG. 3, i.e., regions 301H, 302H, 303H, 305H, 306H. In this example, other information options region 306H is the same as region 306A (FIG. 7) and that description is incorporated by reference herein. Another information options region 2201 includes links to sign up, login, help, feedback, and my account.

In stent-graft planning progress guide region 301H, four steps are again illustrated, aneurysm measurement step 1, physician's options step 2, graft selection step 3, and online order step 4. Order online step 4 is still highlighted.

Data input region 303H includes confirmation of the submitted order and a print button 2253. If the user selects print button 2253, the order form illustrated in FIGS. 21A and 21B is printed.

Navigation region 305H of online order graphic user interface 2210 includes a sign out button 2251, and create new stent-graft button 2252. Both buttons functions as described above for similarly named buttons and that description is incorporated herein by reference.

If the user at anytime clicks on the my account link, my account graphic user interface 2310 (FIG. 23) is displayed on display 400. My account graphic user interface 2310 includes the regions as described above for FIG. 3, i.e., regions 303I, 306I. In this example, other information options region 306I is the same as region 306A (FIG. 7) and that description is incorporated by reference herein. Another information options region 2301 includes links to sign up, login, help, feedback, and my account.

Data input region 303I includes change links for login name, login password, e-mail address, and hospital name. If the user selects one of these links, a pop-up window is presented in which the user makes and confirms the change.

A default for over sizing the aorta stent-graft diameter, and a default for over sizing the iliac stent-graft diameter are presented along with a change link for each. The physician can change these values, using a pop window generated in response to selecting the corresponding change link, to one of the permitted percentages of over sizing. The values on this page are used as default values in the stent-graft selection process, as described above. Check box 2351 is checked if the physician wants to receive follow-up e-mail remainders for each patient. There is also an option for enabling the help pop-up windows that were described above.

Figure 24:
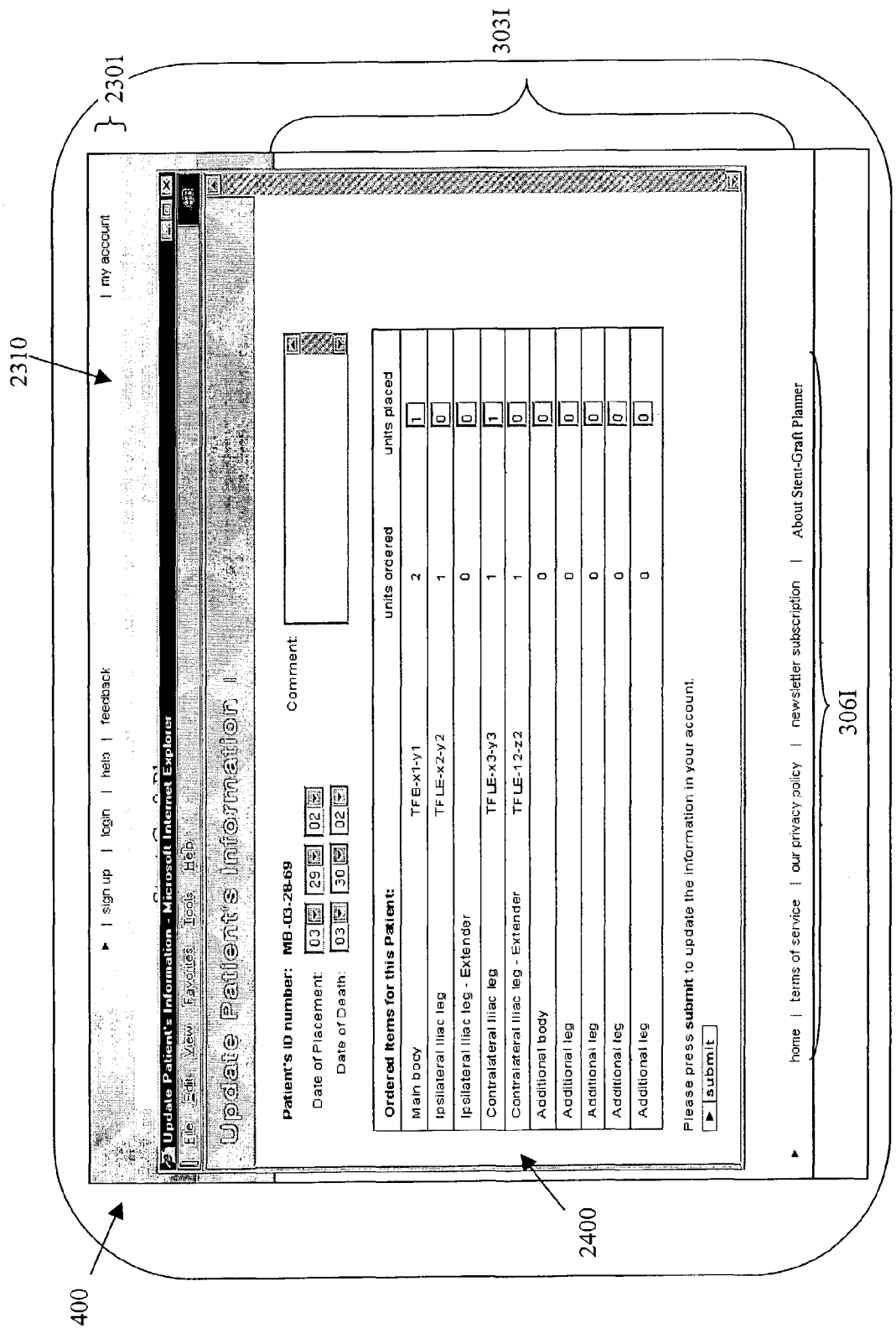
FIG. 24 is an example of an update patient's information pop-up window.

Finally, there is a list of treated patient information. For each patient there is an update link. If the user selects an update link, a pop-up window for that patient is presented. Pop-up window 2400 (FIG. 24) is an example of a layout of the patient information. The physician's information and patient information is stored in physician database 111.

Figure 25A:
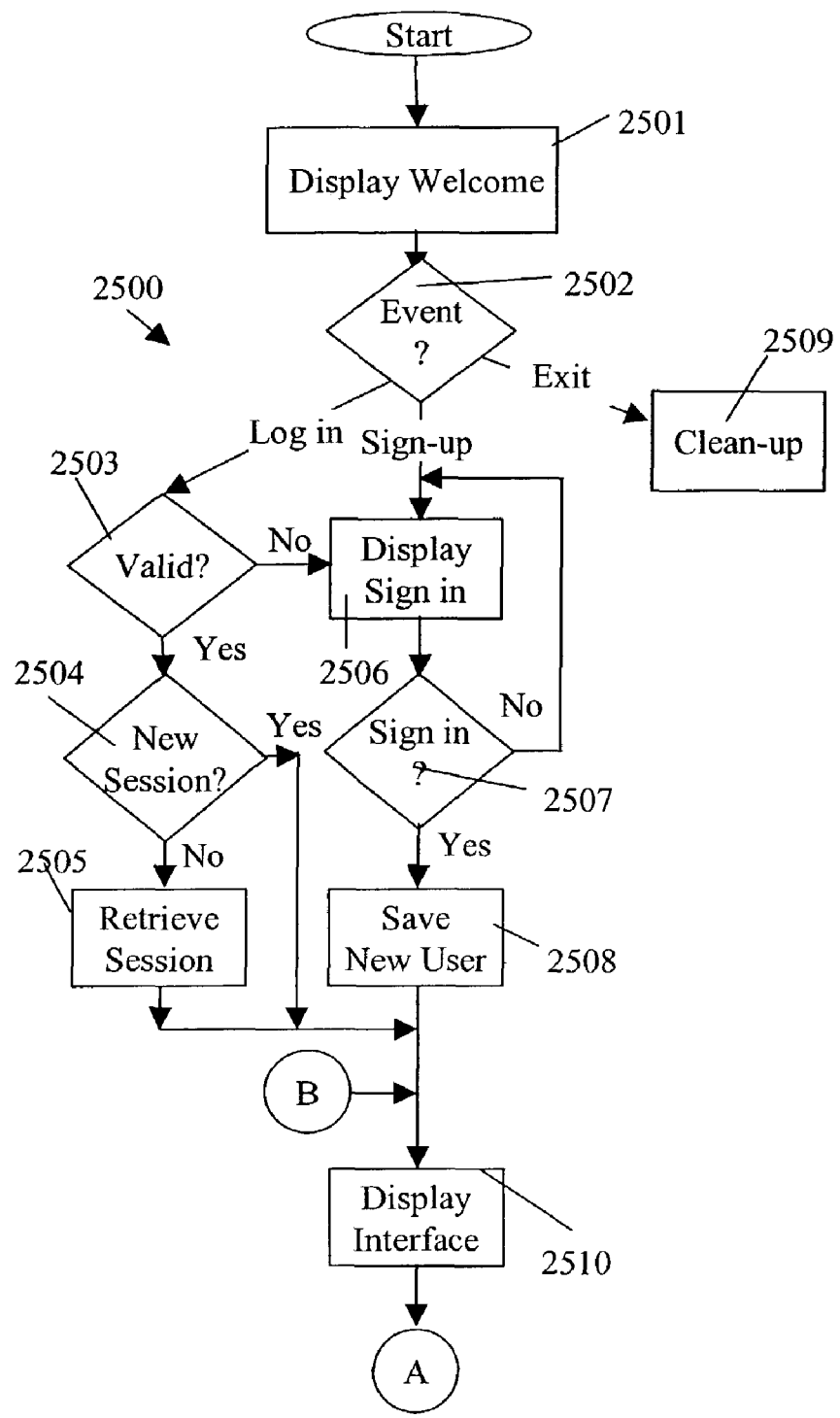
FIGS. 25A and 25B are one example of a more detailed process flow diagram for the process of FIG. 2.
Figure 25B:
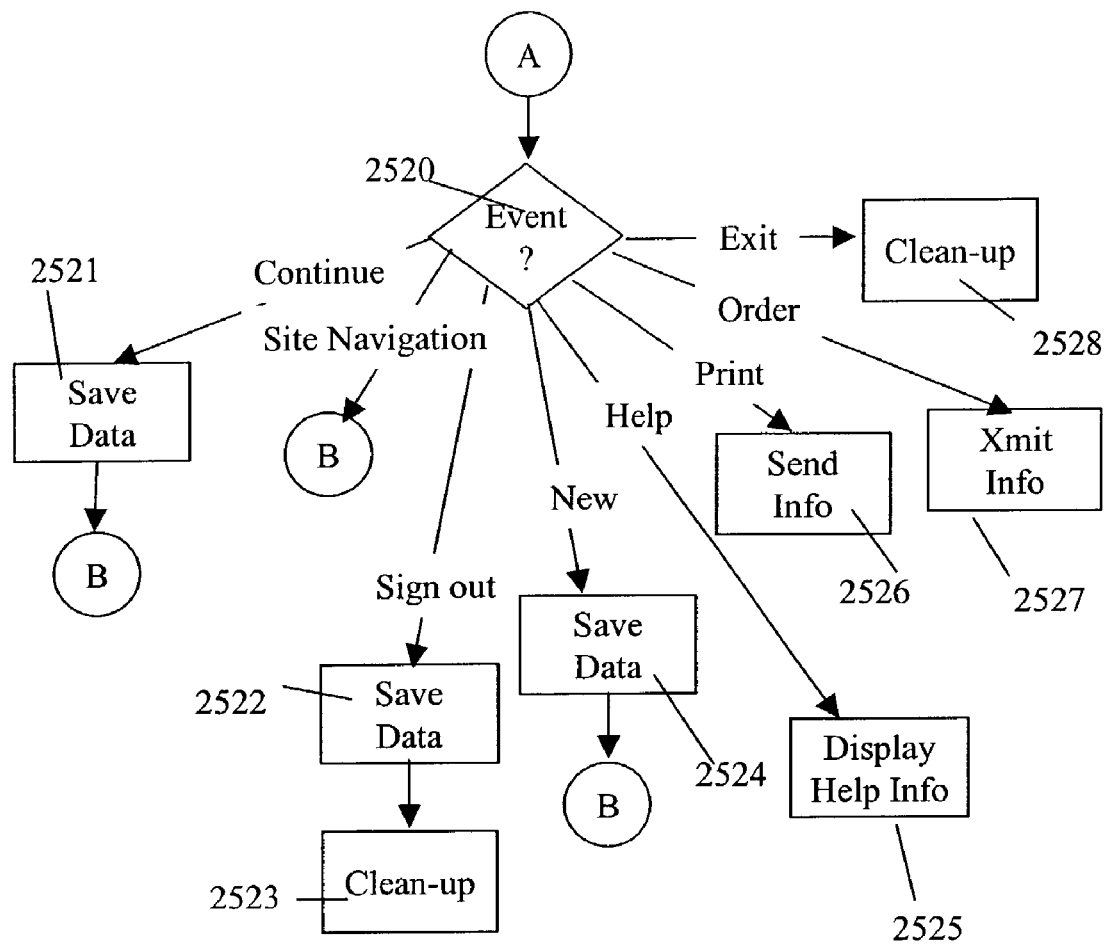

FIGS. 25A and 25B are a more detailed process flow diagram 2500 for stent-graft planning process 200 which is generated by execution of a part of stent-graft planner module 113. When a user accesses the stent-graft planner site, display welcome operation 2501 presents opening graphic user interface 410. Event check operation 2502 is performed by an event handler on the user's device that is typically associated with a web-browser, such as Microsoft's Internet Explorer. The event handler receives a login event, a sign up event, or an exit event, for example.

The login event is generated in response to the use filling in the user name and password and selecting the enter button. If the user selects some other part of the interface, a sign-up event is generated. If the user leaves the site, the exit event is generated. In response to either the sign-up or the login events, a secure connection is established with the user so that no physician or patient information can be compromised.

In response to a login event, event check operation 2502 transfers processing to valid check operation 2503. Valid check operation 2503 compares the login data with data from physician database to determine whether the login data is valid. In one example, the physician and patient information in physician database 111 is encrypted and stored on a non-volatile memory, e.g., a hard disk drive. When data is requested from physician database 111, a portion of the database is moved to volatile memory and decrypted. This is done so that should someone illegally access physician database 111 directly via Internet 104 or network 105, the data is still secure.

If the login data is valid, valid check operation transfers to new session check operation 2504 and otherwise to display sign in operation 2506 that is described below. New session check operation 2504, using information stored in physician database 111, determines whether on a previous visit, the physician signed out without completing a stent-graft selection and/or a stent-graft order.

If there is not an incomplete session, new session check operation is true and so operation transfers to display interface operation 2510 that in turn displays aneurysm proximal neck graphic user interface 710. If there is an incomplete prior session, new session check operation 2504 presents a pop-up window asking whether the user wants to continue with a prior session or continue with a new session.

If the user selects a new session, new session check operation 2504 transfers to display interface operation 2510 that in turn displays aneurysm proximal neck graphic user interface 710. If the user selects continue with a prior session, new session check operation 2504 determines whether the physician has more than one incomplete session. If there is more than one incomplete session, a list of incomplete sessions each with a unique identifier that the physician previously provided is presented in another pop-up window, and the physician is asked to select the incomplete session desired. Thus, there is only one incomplete session or there is a selected incomplete session, and new session check operation 2504 transfers to retrieve session operation 2505.

Retrieve session operations 2505 retrieves from database 111 all the data and warnings saved in the prior session and an indicator of the graphic user interface that was being used when the prior session was terminated. This information is transferred to display interface operation 2510 that in turn displays the graphic user interface indicated and the data and warning information are stored in appropriate locations.

In response to a sign-up event, event check operation 25002 transfers to display sign-in operation that in turn displays a login graphic user interface 510. If the user completes the login box, processing transfers via event check operation 2502 to valid check operation 2503. If the user selects sign up button 521, sign up graphic user interface 610 is presented. If the user exits, event check operation 2502 transfers to clean-up operation 2509. If the user completes the interface, operation 2506 transfers to sign in check operation 2507.

If the user completed the sign-in correctly, sign in check operation 2507 transfers to save new user information 2508. Otherwise, sign in check operation 2507 returns to display sign in operation 2506 that in turn highlights the incorrect or needed information.

Save new user information 2508 saves the entered information in physician database 111. When the information is saved, processing transfers to display interface operation 2510 that in turn displays aneurysm proximal neck graphic user interface 710.

When processing transfers to clean-up operation 2509, any information that is still in volatile memory and should be saved is transferred to database 111. Clean-up operation 2509 performs any other necessary operations to terminate the user-session.

When a user is in a stent-graft planner graphic user interface, as described above, the user can select options that can generate a continue event, a site navigation event, a sign out event, a new session event, a help event, a print event, an order event, or an exit event, for example.

When event check operation 2520 in the event handler receives a continue event, processing transfers to save data operation 2521. Save data operation 2521 saves the data entered in the graphic user interface that was just completed and transfers to display interface operation 2510 that in turn displays the next graphic user interface in the sequence.

When event check operation 2520 (FIG. 25B) in the event handler receives a site navigation event, processing transfers to display interface operation 2510 that in turn displays the page associated with the link activated. When event check operation 2520 in the event handler receives a sign out event, processing transfers to save data operation 2522. Save data operation 2522 is the same as save data operation 2521 and that description is incorporated herein by reference. However, save data operation 2522 transfers processing to clean-up operation 2523 that is the same as clean-up operation 2509 and that description is incorporated herein by reference.

When event check operation 2520 in the event handler receives a new session event, processing transfers to save data operation 2524. Save data operation 2524 saves the data entered in the graphic user interface that was just completed and transfers to display interface operation 2510 that in turn displays aneurysm proximal neck graphic user interface 710

When event check operation 2520 in the event handler receives a help event, processing transfers to display help info operation 2525. Help info operation 2525 retrieves the requested help information from module 113 and displays that information in a pop-up window, as described above.

When event check operation 2520 in the event handler receives a print event, processing transfers to send information operation 2526. Send information operation 2526 retrieves any needed information and sends the information to a printer.

When event check operation 2520 in the event handler receives an order event, processing transfers to transmit information operation 2527. Transmit information operation 2527 retrieves any needed information and transmits the order to the manufacturer of the stent graft selected.

When event check operation 2520 in the event handler receives an exit event, processing transfers to clean-up operation 2528. Clean-up operation 2528 is the same as clean-up operation 2509 and that description is incorporated herein by reference.

The process flow diagrams should not be interpreted as requiring multiple different save and clean-up routines. The multiple operations are shown as being different for clarity. However, those of skill in the art will also appreciate that a single module can be called to perform each of the operations with the same name. Also, the process of FIGS. 25A and 25B is illustrative only and are not intended to limit the invention to only the sequences, operations or events described. In view of this disclosure, one of skill in the art can implement the stent-graft planning process in a wide variety of ways.

Figure 26:
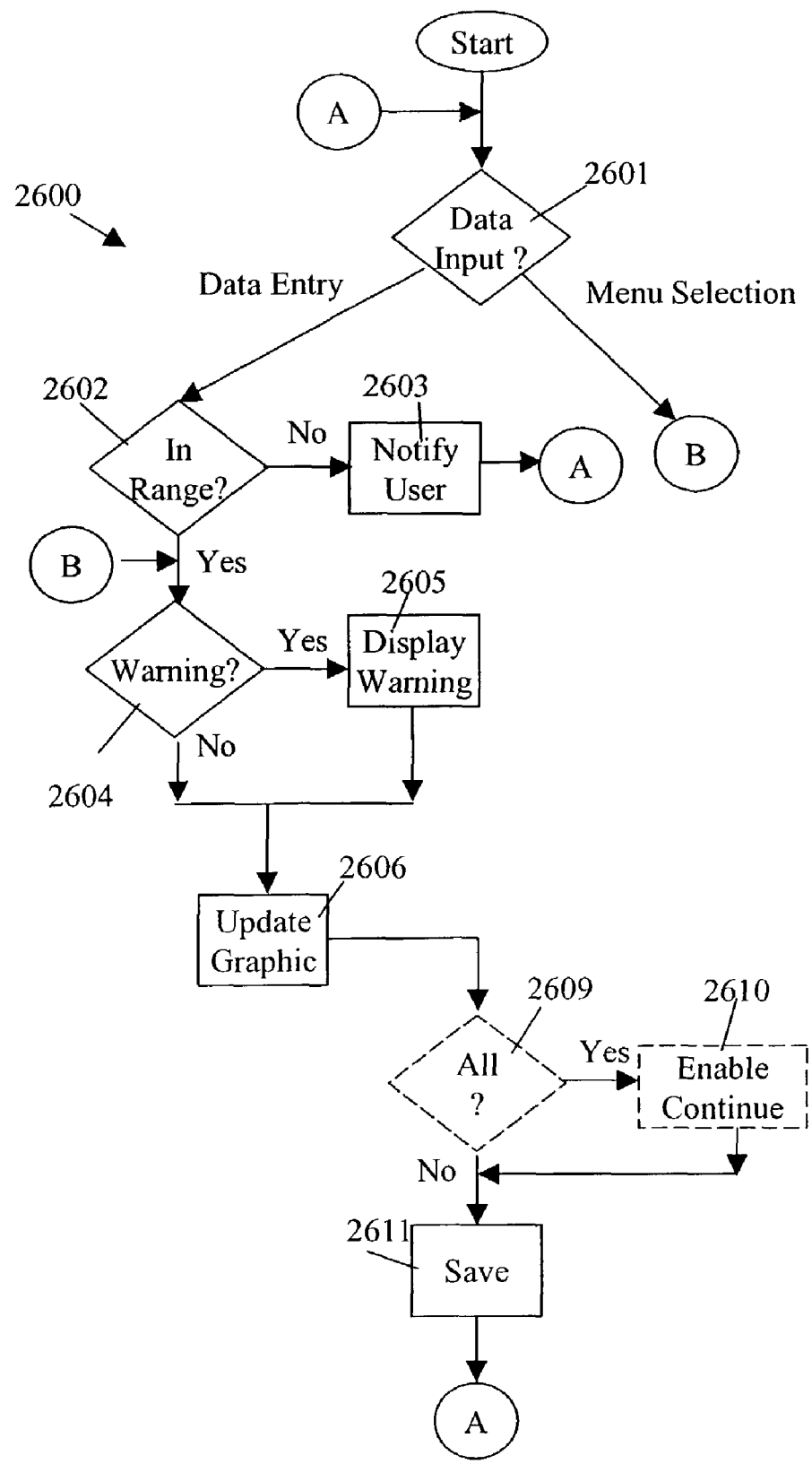
FIG. 26 is an example of a process flow diagram for validation and generating warnings upon data entry.

FIG. 26 is a process flow diagram for a method of data handling 2600 in the graphic user interfaces described above. Data input check operation 2601 is part of an event handler. When the user completes a data entry, a data entry event is generated and data input check operation 2601 transfers to an in range check operation 2602.

In range check operation 2602 determines whether the entered data is within a valid range for the stent-graft parameter. If the data is in the valid range processing transfers to warning check 2604. If the data is not in the valid range, processing transfers to notify user operation 2603, Notify user operation 2603 places the cursor back in the window for the data entry, flags the entry, and provides a message, as described above to the user. Processing stops at this point until another data entry event occurs.

Warning check operation 2604 determines whether the value of the entered data, or the value of the entered data in view of other data requires a warning to the user. For example, the value is checked to determine whether the value is within a range associated with a warning for the stent-graft planning process. If a warning is necessary, processing transfers to display warning operation 2605 and otherwise to update graphic operation 2606.

Display warning operation 2605 generates a pop-up warning window as described above. If the user accepts the warning, operation 2605 transfers to update graphic operation 2606.

Update graphic operation 2606 determines whether the data entry requires an update to the graphic displayed on the graphic user interface. If an update is needed, operation 2606 performs the operation and transfers to all check operation 2609. If no update is needed, operation 2606 transfers directly to all check operation 2609.

All check operation 2609 is optional. In the above embodiment, the continue button on a graphic user interface was not activated until all the data was entered. All check operation 2609 and enable continue operation 2610 perform these operations. However, in another example, the continue button was always active, i.e., could be selected at any time and so operations 2609 and 2610 are not needed. Operations 2609 and 2610 are enclosed with dotted lines to show that the operations are optional.

Save operation 2611 saves the entered data and an any warning or warnings in temporary storage. Alternatively, save operation 2611 could write this information directly to database 111.

If a user selects a data value from a pull down menu, a menu selection event is generated. In this case, data input check 2601 transfers to warning check operation 2604 and processing continues in the same manner as described above for a data entry.

Thus, data for each parameter used in the graft selection process is checked for validity. Also, after each entry, a warning if generated if needed. The data and warnings are also saved. Thus, there is on line capture of measurements; realtime visualization of the measured aneurysm; storage of data capture in database; an integrated warning system; an integrated manufacturer recommendation system; and an invalid data check.

The particular configuration of system 100 is not essential to this invention. In general, the client system can be a mobile telephone, a two-way pager, a portable computer, an Internet appliance, a workstation, or perhaps a personal computer. The client and server can be interconnected by a local area network, a wide area network, or the Internet.

In this example, a client server system has been illustrated. However, the stent-graft planning process can be implemented also on stand-alone devices.

Those skilled in the art will readily understand that the operations and actions described herein represent actions performed by a CPU of a computer in accordance with computer instructions provided by a computer program. For example, a browser program such as Microsoft Internet Explorer, Microsoft Active Server Pages, a SQL database, and Macromedia's Flash can be used to implement an example of this invention.

Therefore, stent-graft planning process can implemented by computer program modules causing the CPU of the computer to carry out instructions representing the individual operations or actions as described herein. The computer instructions can also be stored on a computer-readable medium, or they can be embodied in any computer-readable medium.

Thus, all or part of the present invention can be implemented by a computer program comprising computer program code or application code. This application code or computer program code may be embodied in any form of a computer program product. A computer program product comprises a medium configured to store this computer-readable code, or in which this computer-readable code may be embedded. Some examples of non-transitory computer program products are CD-ROM discs, ROM cards, floppy discs, magnetic tapes, computer hard drives, and servers on a network.

The storage mediums used to the store the databases and the program modules may belong to the user device itself. However, the storage medium also may be removed from the user device as illustrated in FIG. 1.

Herein, a computer memory refers to a volatile memory, a non-volatile memory, or a combination of the two in any one of these devices. Similarly, a computer input unit and a display unit refer to the features providing the required functionality to input the information described herein, and to display the information described herein, respectively, in any one of the aforementioned or equivalent devices.

Further, those of skill in the art will appreciate that while databases 111, 114, and stent-graft planner module 113 are illustrated as single units in a common structure, these units can include both volatile memory and non-volatile memory in most computer systems, and can be distributed across multiple computer systems. The storage medium may be removed from the computer system executing module 113 and using the data in databases 111, 114, and may be connected to that computer system via a data line or a network.

In more general terms, stent-graft planner module 113 is stored in a computer-readable medium, and when module 113 is loaded from the computer-readable medium into a memory of a device, the device is configured to be a special purpose machine that executes all or part of module 113.

Also, in the context of the present invention, system 100 may also comprise a server and a client, which share the above described tasks of the system among themselves. For example, module 113 may be stored and executed on the server. However, the user input data typically is first received by the client, for example, a laptop or handheld computer, an Internet appliance, or a mobile phone. The validation and warning operations could be performed by the client. The remaining operations can be executed by the server, and then the data saved on either the server or the client device. In view of this disclosure, those of skill in the art can appropriate the tasks between a client and a server to achieve the best performance for a given configuration.

The above examples were for an aortic aneurysm in a human body. However, in view of this disclosure, the stent-graft planning process can be used to select a stent graft for placement in any location in a set of vessels in a human or animal body where a stent graft is used. The graphic user interfaces would be modified to collect measurements for the set of vessels that are needed to select a stent graft used in the set of vessels. The measurement collection, validation and warnings would be implemented based upon manufacturer data and scientific knowledge for the stent graft or grafts that could be selected. Therefore, the above examples are illustrative only and are not intended to limit the invention to the specific examples used.

I claim:

1. A computer system comprising:
a stent-graft planner module wherein execution of said stent-graft planner module on said computer system generates a plurality of graphic user interfaces used to collect data for stent-graft selection in a stent graft planning process, wherein at least one of the graphic user interfaces comprises:
a real-time graphic region for displaying a graphic used in said stent-graft planning process, wherein said stent graft planning process is for assisting in selecting a stent-graft for a patient; and
a data entry region for an active stent-graft planning step wherein following entry of measurement data for said active stent-graft planning step in said data entry region, said graphic is modified to reflect the measurement data;
a physician database wherein said physician database includes physician preferences for said stent-graft planning process, wherein said stent graft planning process is for assisting in selecting a stent-graft for a patient; and
a stent-graft database wherein stent-graft database includes manufacturer information for at least one stent graft.

2. The system of claim 1 wherein said computer system is a client-server system.

3. The system of claim 1 wherein said computer system is a stand-alone system.

4. A computer based stent graft planning method comprising:
collecting measurements of vessels in a body, from a user of the stent graft planning method, using a plurality of graphic user interfaces generated by executing a stent graft planner module, wherein at least one of the plurality of graphic user interfaces includes:
a real-time graphic region for displaying a graphic used in said stent-graft planning method, wherein said stent graft planning method is for assisting in selecting a stent-graft for a patient; and
a data entry region for an active stent-graft planning step wherein following entry of measurement data for said active stent-graft planning step in said data entry region, said graphic is modified to reflect the measurement data; and
suggesting automatically a stent graft for use in said vessels using said measurements of vessels, using a physician database including physician preferences for use in said method, and using a stent graft database including manufacturer information for at least one stent graft.

5. The method of claim 4 further comprising:
validating said measurements prior to said using said measurements.

6. The method of claim 4 wherein said vessels are associated with an aortic aneurysm.

7. The method of claim 4 further comprising:
illustrating said vessels via a graphic of said vessels in the graphic region in the at least one of said plurality of graphic user interfaces.

8. The method of claim 7 further comprising:
highlighting a portion of said graphic that corresponds to a measurement to be entered via a data entry window in one of said graphic user interfaces.

9. The method of claim 7 further comprising:
displaying a dimension arrow on a portion of said graphic that corresponds to a measurement to be entered via a data entry window in one of said graphic user interfaces.

10. The method of claim 7 further comprising:
including an image of said stent graft in said graphic.

11. The method of claim 4 wherein said collecting measurements further comprises:
validating at least one of said measurements as being in a range acceptable for use with said stent graft.

12. The method of claim 4 wherein said collecting measurements further comprises:
generating a warning when a measurement indicates a problem with use of said stent graft.

13. The method of claim 4 further comprising:
storing said measurements in a database.

14. The method of claim 4 further comprising:
generating an order that is transmitted via a computer network to a manufacturer of said stent graft.

15. The method of claim 14 wherein said computer network is an Internet.

16. The method of claim 4 further comprising:
changing said stent graft via at least one graphic user interface.

17. The method of claim 4 further comprising:
collecting physician's options, for said physician's database, using another graphic user interface; and
generating an order that is transmitted via a computer network to a manufacturer of said stent graft.

18. The method of claim 17 further comprising:
changing said stent graft via the at least one graphic user interface.

19. The method of claim 17 further comprising:
validating said measurements prior to said using said measurements.

20. The method of claim 17 wherein said vessels are associated with an aortic aneurysm.

21. The method of claim 17 further comprising:
illustrating said vessels via a graphic of said vessels in the graphic region in the at least one of said plurality of graphic user interfaces.

22. The method of claim 21 further comprising:
changing said graphic of said vessels to reflect said measurements.

23. The method of claim 21 further comprising:
highlighting a portion of said graphic that corresponds to a measurement to be entered via a data entry window in one of said graphic user interfaces.

24. The method of claim 21 further comprising:
displaying a dimension arrow on a portion of said graphic that corresponds to a measurement to be entered via a data entry window in one of said graphic user interfaces.

25. The method of claim 21 further comprising:
including an image of said stent graft in said graphic.

26. The method of claim 17 wherein said collecting measurements further comprises:
validating at least one of said measurements as being in a range acceptable for use with said stent graft.

27. The method of claim 17 wherein said collecting measurements further comprises:
generating a warning when a measurement indicates a problem with use of said stent graft.

28. The method of claim 17 further comprising:
storing said measurements in a database.

29. The method of claim 17 wherein said computer network is an Internet.

30. The method of claim 17 further comprising:
generating a follow-up message for a physician.

31. A non-transitory computer program product having stored thereon computer readable computer code wherein execution of said computer readable computer code generates a method comprising:

collecting measurements of vessels in a body, from a user of the stent graft planning method, using a plurality of graphic user interfaces generated by executing a stent graft planner module, wherein at least one of the plurality of graphic user interfaces includes:
- a real-time graphic region for displaying a graphic used in said stent-graft planning method, wherein said stent graft planning method is for assisting in selecting a stent-graft for a patient; and
- a data entry region for an active stent-graft planning step wherein following entry of measurement data for said active stent-graft planning step in said data entry region, said graphic is modified to reflect the measurement data; and suggesting automatically a stent graft for use in said vessels using said measurements of vessels, using a physician database including physician preferences for use in said method, and using a stent graft database including manufacturer information for at least one stent graft.

32. The non-transitory computer program product as in claim 31 wherein said method further comprises:
- collecting physician's options, for said physician's database, using at least one graphic user interface; and
- generating an order that is transmitted via a computer network to a manufacturer of said stent graft.

* * * * *